(12) United States Patent
Hu

(10) Patent No.: US 10,689,421 B2
(45) Date of Patent: Jun. 23, 2020

(54) **BACTERIOCIN-PRODUCING *PAENIBACILLUS EHIMENSIS* AND APPLICATION THEREOF**

(71) Applicant: National Pingtung University of Science and Technology, Pingtung County (TW)

(72) Inventor: Shao-Yang Hu, Pingtung County (TW)

(73) Assignee: National Pingtung University of Science and Technology, Pingtung County (TW)

( * ) Notice: Subject to any disclaimer, the term of this patent is extended or adjusted under 35 U.S.C. 154(b) by 64 days.

(21) Appl. No.: 15/936,443

(22) Filed: Mar. 27, 2018

(65) Prior Publication Data

US 2019/0241620 A1    Aug. 8, 2019

(30) Foreign Application Priority Data

Feb. 2, 2018    (TW) .............................. 107103899 A

(51) Int. Cl.
| | | |
|---|---|---|
| *C07K 14/195* | (2006.01) | |
| *A23L 33/135* | (2016.01) | |
| *A23L 3/3463* | (2006.01) | |
| *A01N 37/46* | (2006.01) | |
| *A01N 63/10* | (2020.01) | |

(52) U.S. Cl.
CPC ............ *C07K 14/195* (2013.01); *A01N 37/46* (2013.01); *A01N 63/10* (2020.01); *A23L 3/34635* (2013.01); *A23L 33/135* (2016.08); *C12N 2330/10* (2013.01)

(58) Field of Classification Search
CPC ...................................................... A23K 50/80
See application file for complete search history.

(56) References Cited

PUBLICATIONS

Biocontrol of Meloidogyne incognita inciting disease in tomato, Seong H. Hong et al., https://doi.org/10.1080/09583157.2013.811468, Jun. 11, 2013.
Immune responses and enhanced disease resistance in Chinese drum, X Pan et al., Journal of Fish Diseases 2008, 31, 679-686.
Influence of probiotic feeding duration on disease resistance and immune parameters in rainbow trout, S.M. Sharifuzzaman et al., Fish & Shellfish Immunology 27 (2009) 440-445, Jun. 23, 2009.
Isolation and partial characterization of cyclic lipopeptide antibiotics produced by Paenibacillus ehimensis B7, Zhaohui, Huang et al., http://www.biomedcentral.com/1471-2180/13/87, Apr. 17, 2013.

*Primary Examiner* — Bin Shen
(74) *Attorney, Agent, or Firm* — The Webb Law Firm

(57) ABSTRACT

The present invention relates to a bacteriocin-producing *Paenibocillus ehimensis* strain NPUST-1, which can intensify the growth and immune response of aquaculture organisms. Also, the strain can increase the survival rate of aquaculture organisms after pathogen infection. A bacteriocin produced by the *Paenibocillus ehimensis* strain NPUST-1, Peocin, is a starvation/stationary phase protection protein, which has antimicrobial activity against various pathogen including aquaculture pathogens, foodborne pathogens and clinical pathogens. The bacteriocin Peocin is a starvation/stationary phase protection protein having antimicrobial activity found for the first time.

3 Claims, 20 Drawing Sheets

Specification includes a Sequence Listing.

DEFINITION DNA starvation/stationary phase protection protein [*Paenibacillus chinensis*]

ACCESSION WP_025850494

---

MNEQLTVLLNNQIANWSVLYVKLHNYHWYVKGPQFFTLHTKF
EELYTEAALHVDALAERLLALGGKPVATMSGSLRLASVREAEG
EESAERMVAALVNDFTLIIGELKSGMKYAESVQDETTGDLLLAI
HSSLEKHVWMLNAFLGN

Fig. 4

BACTERIOCIN-PRODUCING PAENIBACILLUS EHIMENSIS AND APPLICATION THEREOF

CROSS-REFERENCE TO RELATED APPLICATIONS

The present application claims priority to Taiwanese Patent Application No. 107103899, filed Feb. 2, 2018.

The Sequence Listing associated with this application is filed in electronic format via EFS-Web and is hereby incorporated by reference into the specification in its entirety. The name of the text file containing the Sequence Listing is 1906479_ST25.txt. The size of the text file is 9.783 bytes, and the text file was created on Feb. 17, 2020.

FIELD

During the cultivating of aquaculture organism, general intensive cultivation will cause the rapid spread of pathogen infection, and lead to the mass mortalities of aquaculture organism and further economic losses. The disease is therefore a serious problem that obstructs the development of aquaculture. Currently in the market, antibiotic and chemical products are mainly used to solve the disease problem. However, chemicals are also harmful to non-target organisms, and continuous uses of chemicals are deleterious to human health or environment. Moreover, the abuse of antibiotic would cause drug resistance of pathogens, thus damage the ecological environment. As a consequence, in the view of food safety and environmental sustainability, there is an increasing need for biological control in the recent years.

BACKGROUND

Using probiotics isolated from nature has been an alternative biological control strategy to efficiently prevent disease, which has less effect on the environment, and can reduce the risk of drug resistance of pathogens. Among those probiotics, *Paenibacillus ehimensis* have been applied to control cash crops disease, for instance, *Meloidogyne incognita* and *Fusarium* wilt in tomato (Hong, Anees, & Kim, 2013), or *Phytophthora capsici* in peppers. However, compare to the cash crops mentioned above, the rearing environment of aquaculture organism is more complicated due to factors like water quality, pH change, salinity and symbiotic microorganism. Hence, no application of *Paenibacillus ehimensis* has been taught by prior art in the field of aquaculture.

Bacteriocin, an antibacterial substance that is produced by probiotics, when comparing to other chemical synthesis antibacterial additives and antibiotics, bacteriocin is majorly consisted of proteins such as ribosome or small molecular peptides. It is usually harmless to human and environment, hence, it can be further applied in food industry and clinical medications to alternate with antibiotics as antibacterial substances. Currently it has beenidentified that the bacteriocin produced by *Paenibacillus ehimensis* such as 2 cyclic lipopeptides PE1, PE2 from *P. ehimensis* B7 strain can have clinical antibacterial effect on antibiotic resistant bacteria such as *Methicillin*-resistant *Staphylococcus aureus* (MRSA), *E. coli, P. aeruginosa* (Z. Huang et al., 2013); bacteriocin polypeptin C identified from *P. ehimensis* MA2012 can inhibit phytopathogenic fungi and bacterial pathogen (Kyaw Wai Naing et al., 2015). However, the patents or researches regarding application of bacteriocin produced by *Paenibacillus ehimensis* has not yet been disclosed in the field of aquaculture.

Moreover, previous studies about probiotics application in aquaculture were mainly investigation of the ability of probiotics in promoting aquaculture organism growth and disease resistance. However, in recent years, the immunoregulation of probiotics for aquaculture organism has been concerned. The effect of probiotics elevating the immunoregulation for aquaculture organism has been disclosed. For example, *Clostridium butyricum* can elevate the expression of lysozyme, phagocytizing activity and immunoglobulin in *Miichthys miiuy*, and survival rate of *Miichthys miiuy* infected with *Vibrio anguillarum; Kocuria* species can elevate the expression of lysozyme, phagocytizing activity and immunoglobulin in *Oncorhynchus mykiss*, it also elevate the survival rate of *Oncorhynchus mykiss* infected with *Vibrio anguillarum*. (Sharifuzzaman & Austin, 2009).

RELATED BACKGROUND ART OF THE INVENTION

Non-Patent Documents

Hong, S. H., Anees, M., and, K. Y. 2013. Biocontrol of *Meloidogyne incognita* inciting disease in tomato by using a mixed compost inoculated with *Paenibacillus ehimensis* RS820. Biocontrol Science and Technology, 23(9), 1024-1039.

Huang, Z., Hu, Y., Shou, L., & Song, M. 2013. Isolation and partial characterization of cyclic lipopeptide antibiotics produced by *Paenibacillus ehimensis* B7. BMC Microbiology, 13(1), 87.

Pan, X., Wu, T., Song, 2., Tang, H., & Zhao, Z. 2008. Immune responses and enhanced disease resistance in Chinese drum, *Miichthys miiuy* (Basilewsky), after oral administration of live or dead cells of *Clostridium butyrium* CB2. Journal of Fish Diseases, 31(9), 679-686.

Sharifuzzaman, S. M., & Austin, B. 2009. Influence of probiotic feeding duration on disease resistance and immune parameters in rainbow trout. Fish & Shellfish Immunology, 27(3), 440-445.

SUMMARY

The Problems that the Invention Aims to Solve

In summary, in the field of aquaculture, there is the demand to develop bacteriocin-producing probiotics that can substitute antibiotics and chemical agent. In the meantime, considering the development requirement of great amount of time and monetary cost, it is also anticipated that the bacteriocin produced by probiotics has antibiotic activity against many pathogens, or that this probiotics has the efficacy to improve aquaculture organism immune response, thus the probiotics can be widely applied to prevention of multiple disease. Furthermore, to achieve higher productivity, it is also anticipated that this probiotics has the efficacy to promote aquaculture organism growth.

Hence, this invention aims at providing a bacteriocin-producing probiotic which can be applied in the field of aquaculture. It is expected that the provided probiotic is a probiotic which can be used to improve aquaculture organism immunity, and it is also expected that the bacteriocin produce by the said probiotic has antibiotic activity against many pathogens. Moreover, it is expected that this probiotics has the efficacy to promote aquaculture organism growth.

Technical Means

The inventors of the present invention carry out in-depth studies in view of the foresaid issues and successfully isolated the bacteriocin-producing *Paenibacillus ehimensis* strain NPUST-1 from tilapia culture pond, furthermore, the bacteriocin, Peocin, is purified and analyzed. The immune reaction of zebrafish and tilapia fed with *Paenibacillus ehimensis* strain NPUST-1 is analyzed. Thus providing the bacteriocin-producing *Paenibacillus ehimensis* strain NPUST-1, which can promote the aquaculture organism growth and immune reaction. Meanwhile, the provided strain can also increase the survival rate of aquaculture organism after infected by pathogens.

Moreover, the bacteriocin-producing Peocin produced by *Paenibacillus ehimensis* strain NPUST-1 is a DNA starvation/stationary phase protection protein, which has antibacterial effect on aquaculture pathogenic bacteria, foodborne pathogenic bacteria and clinical pathogenic bacteria. This bacteriocin Peocin is the first starvation/stationary phase DNA protection protein to be seen with antibacterial effect.

A *Paenibacillus* strain NPUST-1 identified as *Paenibacillus ehimensis*, wherein said strain is deposited in CCTCC (China Center for Type Culture Collection) in China, under the deposition number M2018074, the date of deposition is 24 Jan. 2018; also deposited in Food Industry Research and Development Institute in Taiwan, under the deposition number BCRC 910802, the date of deposition is 14 Nov. 2017.

In one example, the strain can promote aquaculture organism growth and immunity.

In one example, the strain can be used as a probiotic to feed aquaculture organism.

According to another aspect of the present disclosure there is provided a bacteriocin protein, wherein said bacteriocin protein is a DNA starvation/stationary phase protection protein produced by *Paenibacillus ehimensis* (deposit number M2018074) and have amino acid SEQ ID NO: 1.

In one example, the bacteriocin protein has antibacterial effect on aquaculture pathogens, food borne pathogens and clinical pathogens.

In one example, the aquaculture pathogens, food borne pathogens and clinical pathogens includes: *Aeromonas hydrophila, Vibrio vulnificus, Vibrio alginolyticus, Vibrio parahaemolyticus, Streptococcus agalactiae, Debaryomyces hansenli, Staphylococcus aureus,* Methicillin-resistant *Staphylococcus aureus*(MRSA), *Escherichia coli, Salmonella typhimurium, Usteria monocytogenes, Pseudomonas aeruginosa,* and *Burkholderia gladioli*.

In one example, the bacteriocin protein can be used as natural antimicrobial agent in food or cosmetics.

In one example, the bacteriocin protein can be used as a protein drug substituting antibiotics in therapy for infection of pathogen with drug resistance.

According to another aspect of the present disclosure there is provided an aquaculture organism feed, wherein the diet formulation of the said feed comprises the *Paenlbacillus ehimensis*.

In one example, the feed can be used to increase the survival rate of aquaculture organisms against *Aeromonas hydrophila* infection.

Advantages of the Invention

The NPUST-1 strain of the present invention can be greatly applied as probiotics for aquaculture organisms, it can increase the feed conversion ratio and feed conversion efficiency, and promote expression of many immune related genes and many important fish immune markers. The strain can promote growth and increase immune reaction at the same time, thus can increase the yield in aquaculture. Meanwhile, the strain has resistance against ampicillin and sulfamerazine, thus can be jointly used in biological control.

The bacteriocin produced by this strain, Peocin, has antibacterial effect on many pathogenic bacteria comprising aquaculture pathogens, foodborne pathogens and clinical pathogens. Peocin has application potential in various fields such as aquaculture, food, clinical medicine, agriculture disease prevention. Moreover, this bacteriocin Peocin has tolerance toward high temperature, pH value, protease, and can still have 66% antibacterial effect under 40° C. preservation for a long period of time. Accordingly, using this bacteriocin Peocin as natural antibacterial additive not only requires high temperature in feed production process, but also has advantage in heat tolerance, pH value tolerance of product development.

BRIEF DESCRIPTION OF THE DRAWINGS

FIG. 4 coverage ratio of identified NPUST-1 antibacterial protein Peocin and DNA starvation/stationary phase protection protein (SEQ ID NO: 1) by LC/MS analysis.

DETAILED DESCRIPTION

Figure 1:
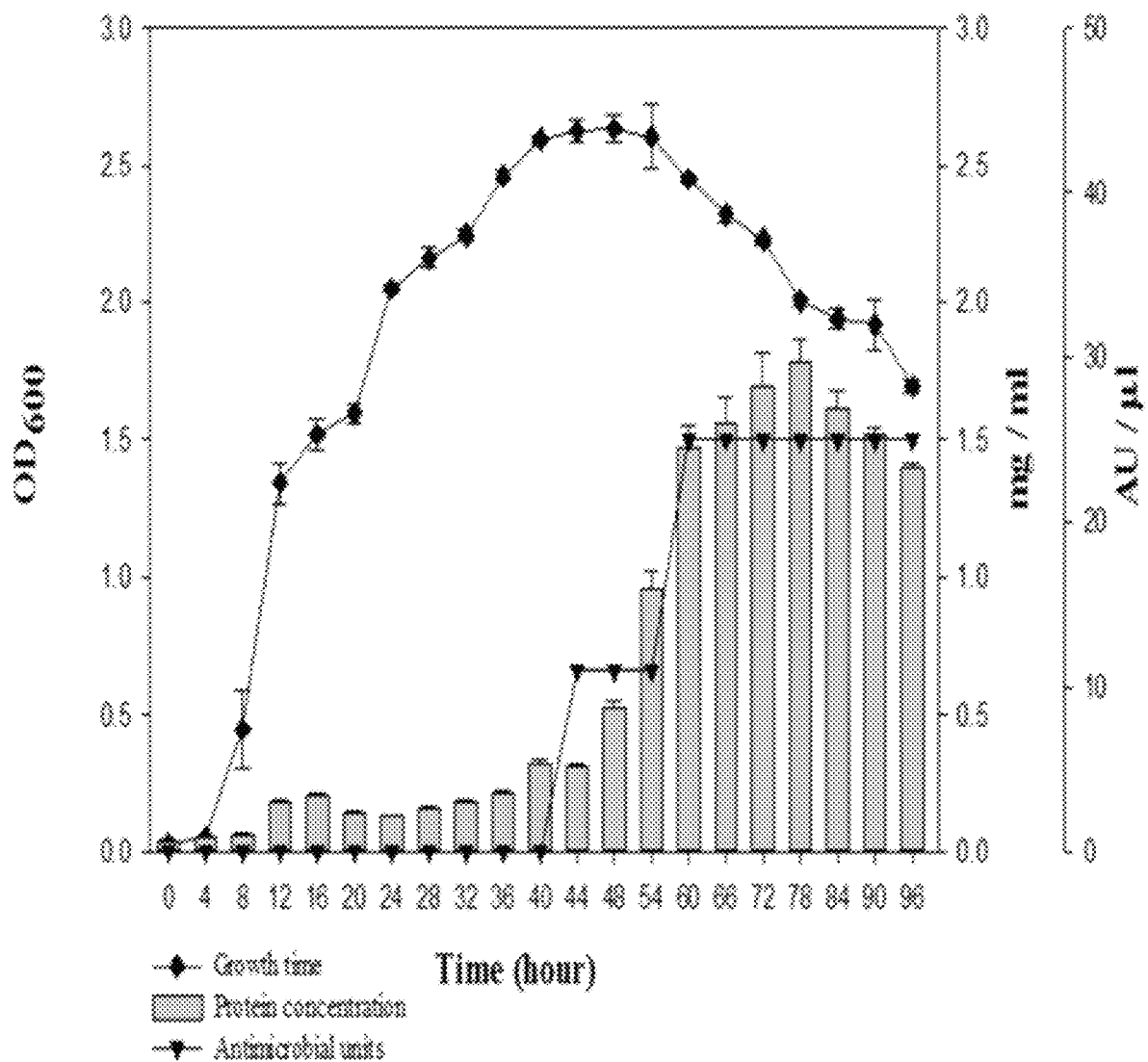
FIG. 1 shows the growth curve, protein concentration, and antimicrobial activity of NPUST-1.

The present invention will be further exemplified by the following examples, which are not to be seen as limiting. The embodiments and description are used for illustrating the details and effect of the present invention.

[Source and Cultivation of the Strain]

Samples were obtained from tilapia aquaculture pool, dilute them to 100 times and spread it on TSB culture plate containing indicator strain *E. coli*. Culture it for four days under 28° C. and observe daily for colony growth and existence of inhibitory zone. Select the colonies with zone of inhibition and screen one single colony using streak-plate method on TSB culture plate. Bioresource Collection and Research Center (BCRC) in Taiwan was entrusted to identify this strain. Based on its 16 s rDNA sequence and biochemistry characteristics, the strain has been identified as *Paenibacillus ehimensis* and named as *Paenibacillus ehimensis* NPUST-1 (hereinafter referred to as "NPUST-1").

[Bacteria Strain Culture and Preservation]

Inoculate *P. ehimensis* NPUST1 culturein flask containing 50 ml TBS culture medium and culture by shake culture for 24 hours in incubation box under 28° C., 175 rpm to obtain revived culture. The following day, collect 1 ml of revived culture and add it in 500 ml flask containing 100 ml TBS culture medium. To create the strain preservation stock, shake culture the culture medium for 24 hours in incubation box under 28° C., 175 rpm, add 0.5 ml of the cultured bacterial liquid into 1.7 ml microcentrifuge tube, add 50% glycerol and mix so the final glycerol concentration would be 25% (v/v). Preserve the stock in –80° C. freezer. To revive for usage, it needs to be cultured in TSB broth culture for 24 hours under 28° C.

[Bacteria Strain Characteristic Assay]

Add the aforementioned –80° C. preserved NPUST-1 into 50 ml TSB broth culture and culture it for 24 hours under 28° C. for reviving. Next, add 1 ml revived culture of NPUST-1 strain into 100 ml fresh TSB broth culture, collect the broth culture regularly to measure the absorbance $OD_{600}$ and illustrate the growth curve, then extract the culture sample necessary for protein concentration determination and antibacterial activity determination. In prior 48 hours, the broth culture is sampled once every four hours, afterwards it is sampled once every six hours.

The protein concentration is examined using protein assay kit (Bio-Rad, USA). The Coomassie brilliant blue G-250 in test reagent changes color when combining with alkaline or aryl amino acid residue of protein, the protein concentration is then determined by absorbance $OD_{595}$ measurement. Bovine serum albumin (BSA) is used as standard group and is prepared into a series of concentration to 0, 20, 40, 60, 80 and 100 μg/ml. 50 μl of each different concentration BSA and NPUST-1 culture samples collected at aforementioned scheduled time were added respectively in 96-well plates. Thereafter, add 200 μl diluted protein concentration assay reagent respectively and place the plate inside drawer to avoid light for 10 minutes. Then, measure absorbance $OD_{595}$. Create a standard curve using the standard group, then estimate the protein concentration of the sample by that standard curve.

Antibacterial activity is evaluated by using Resazurin reduction assay. The Resazurin reduction assay is used to determine bacteria or cell activity, based on its reaction with mitochondria NADH dehydrogenase, which reduces the original dark blue Resazurin into pink Resorufin. Dilute the indicator bacterial strain *E. coli* cultured in advance to $1\times10^7$ CFU/ml and prepare 0.25 mg/ml Resazurin dye for following experiment. 96-well plate was divided into groups of three well as a triplication of one sample set; the total being 21 sets and every well was added with 60 μl TSB medium, 10 μl Resazurin dye, 10 μl indicator strain and 20 μl sample (total 100 μl). The aforementioned 20 μl sample is prepared by adding 0, 1, 2, . . . 20 μl of sample medium respectively, then use TSB medium to fill the total sample volume to 20 μl. Place the sample added 96-well plate in 37° C. incubation box for 12 hours and observe the results. Antibacterial unit (AU) is determined by Resazurin assay, whereas the minimum amount of sample medium required to inhibit color change is 1AU. The antibacterial activity of sampled culture in each time point is represented by how many AU there is in 1 ml of medium.

The growth curve, protein concentration change and antibacterial activity change are drawn on the figure based on sample collection time for comparison. FIG. 1 showed that NPUST-1 goes into stationary phase after culturing for 36 hours. The protein concentration and antibacterial activity gradually increase in broth culture during the later stage of stationary phase. This result indicates that the protein concentration and antibacterial substance in broth culture have positive linear relation, which means the protein NPUST-1 produces has antibacterial activity. In the meantime, antibacterial substance is produced during the later stage of stabilization period and expresses greatly when growth of bacterial strain goes into death phase.

[Purification of Antibacterial Protein]

Purification of antibacterial protein is proceeded using ammonium sulfate precipitation method, which salts out and precipitates antibacterial protein. Ammonium sulfate is a kind of neutral salt and has good stabilizing effect on protein. The principle of this method is using larger ion volume of ammonium sulfate to conjugate with oxidane, causing the protein originally dissolved in water to reveal its non-polar region, the non-polar region will conjugate with each other and the protein will form into a bigger molecule and precipitate. Each kind of protein will precipitate under different maximum concentration level of ammonium sulfate due to different distribution of non-polar region on protein surface. After tested by different concentration of ammonium sulfate (10, 20, 30, 40, 50, 60, 70 and 80), it has been discovered that antibacterial protein will be salted out while ammonium sulfate concentration is at 60%. Therefore, the purification of antibacterial protein in the following is carried out by 60% ammonium sulfate.

Take 500 μl liquid bacteria from –80° C. preserved NPUST-1 strain, add it to 50 ml TSB broth culture and culture it for 24 hours under 28° C. for activation. Next, add 1 ml revived culture of NPUST-1 strain into 100 ml fresh TSB broth culture and culture it for 4 days under 28° C. Transfer the cultured aliquots into 50 ml centrifuge tube and centrifuge them for 20 minutes under 4000 rpm. Transfer the supernatant into beaker, slowly add ammonium sulfate into the beaker over ice until the final concentration reach 60%, wait until the ammonium sulfate is fully dissolved, then place the mixture in 4° C. freezer for 16 hours for the antibacterial protein to salt out. Aliquot the sample after precipitation and transfer them into 50 ml centrifuge tube and centrifuge them at 4° C. for 30 minutes with the speed of 4000 rpm (Eppendorf, 5810R) to separate the antibacterial substance. Add 1 ml PBS (pH 7.4) in precipitated antibacterial substance, transfer the mixture into dialysis membrane and place the membrane in 4° C. freezer for 16 hours, then use 1 L PBS (pH 7.4) buffer for dialysis. The impurities in sample after dialysis is removed using 0.45 µm microfilter, and purified antibacterial protein is obtained and preserved in 4° C. freezer.

Figure 2:
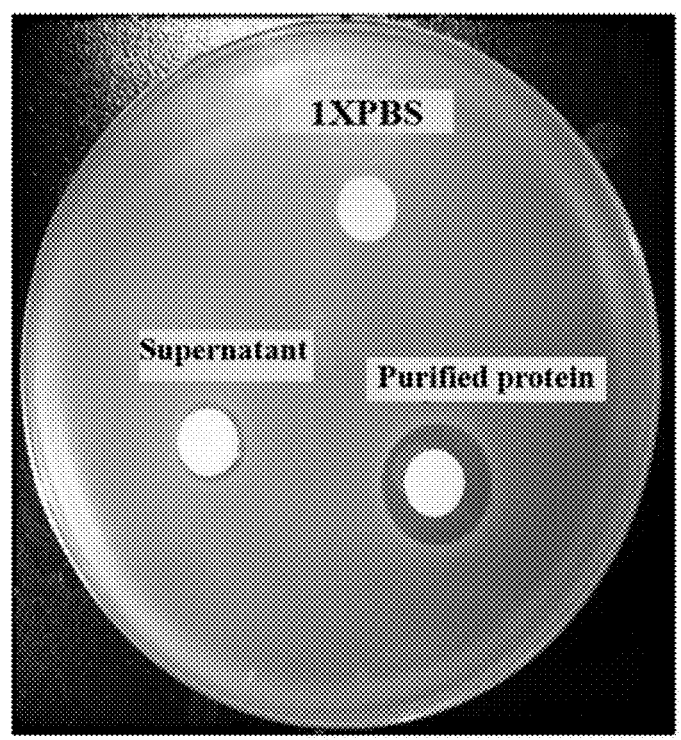
FIG. 2 shows the antibacterial activity of antibacterial protein Peocin from NPUST-1 after purification.

The antibacterial activity determination result of dialysis purified antibacterial sample is shown in FIG. 2, the antibacterial activity after preliminary purification is significantly higher than the unpurified culture supernatant.

[Gel Electrophoresis Analysis of Antibacterial Protein]

Use sodium dodecyl sulfate polyacrylamide gel electrophoresis (SDS-PAGE) analysis along with antibacterial test to determine the antibacterial protein molecular weight of purified antibacterial protein. The steps comprising, first, mix sample and marker with sample buffer respectively, heat the mixture for 10 minutes under 100° C., then place them on ice for 5 minutes, load the sample into SDS-PAGE well and perform gel electrophoresis for 120 minutes at 100 Volt. Stain the SDS-PAGE gel with Coomassie Brilliant Blue R-250 for 30 minutes, then use destaining solution to destain until each band is clearly recognizable. On the other hand, select another SOS-page gel that underwent the electrophoresis with same conditions and wash it with ddH$_2$O 2~3 times to completely remove the remaining running buffer on gel. Slowly place the gel on TSB petri dish containing indicating bacteria strain $E.$ $coli$, culture overnight in 28° C., observe the gel covered area and the transparent bands appearance on medium. Compare the transparent bands with the gel stained with Coomassie Brilliant Blue R-250.

Figure 3:
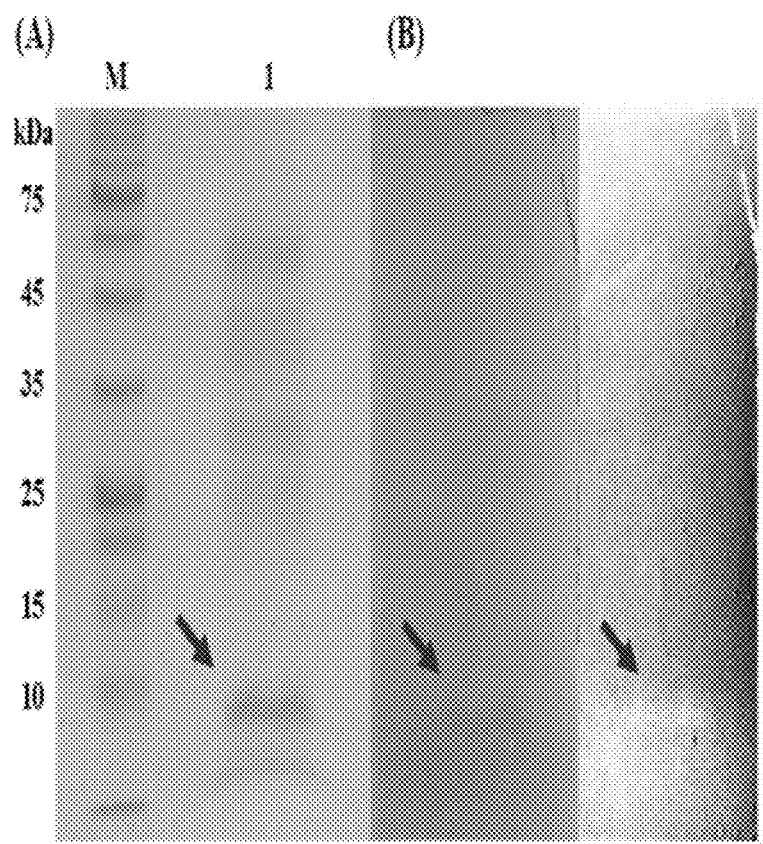
FIG. 3 shows the electrophoresis SDS-PAGE comparative analysis result of antibacterial protein Peocin molecular mass and subsequent agar-overlay bacteriostatic belt result in experiment.

Results shown as FIG. 3, according to the position of arrow indicated band (antibacterial substance) and corresponding marker, the molecular weight of purified antibacterial protein is about 10 kDa.

[Determination of Antibacterial Protein by LC-MS Analysis]

Furthermore, use liquid chromatography and mass spectrometer (LC-MS) to determine the protein identity and molecular weight. First, follow the steps described below to undergo gel digestion: slice the SDS-PAGE gel dyed with Coomassie Brillant Blue R-250 with scalpel, extract the blue band area where the antibacterial substance is, wash with ddH$_2$O, use scalpel to cut out approximately 1 mm$^2$, then wash again with 100 µl ddH$_2$O or 100 µl 25 mM Ammonium bicarbonate (ABC) solution twice, add 100 µl 25 mM ABC buffer containing 50 mM Dithiothreitol (DTT), and place the mixture in 37° C. for an hour for the protein to renature. Next, micro-centrifuge the mixture for 10 seconds, remove the supernatant using pipette, add 100 µl 25 mM ABC buffer containing 100 mM Iodoacetic acid (IAM), stand for 30 minutes at room temperature and avoid light to undergo alkylation. Centrifuge the alkylated sample in micro centrifuge for 10 seconds, remove the supernatant using pipette, add 100 µl 25 mM ABC buffer containing 50% Acetonitrile (ACN), place in ultrasonic cleaner to destain for 15 minutes, after oscillation, centrifuge it at speed of 13000 rpm and repeat this oscillate-centrifuge cycle at least twice until the gel is colorless. Centrifuge the destained sample in microcentrifuge for 10 seconds, remove the supernatant using pipette, add 100 µl 100% ACN and stand for 5 minutes, then extract the liquid and freeze dry it in freeze dryer for 5 minutes. Add 100~150 µl of 25 mM ABC buffer to the frozen dried gel and grind it with pestle in semi-circle from two different direction once respectively, then, use the shaker to shake briefly and use the micro-centrifuge to centrifuge the fragments. Next, add adequate amount of trypsin and stand for 16 hours under 37° C. The ratio of added enzyme:protein=1:20 (enzyme amount=protein weight/resuspend volume (µl)/number of protein bands). After reaction is complete, collect the supernatant of sample and add 100 ml buffer containing 5% Trifluoroacetic acid (TFA), 50% ACN to the remaining gel fragments. Shake in ultrasonic cleaner for 10 seconds and stand for 10 seconds, repeat this procedure for 10 times and centrifuge the mixture at speed of 13000 rpm for 2 minutes, then collect the supernatant (repeat this centrifuge-collect supernatant steps for 3 times).

Figure 5:
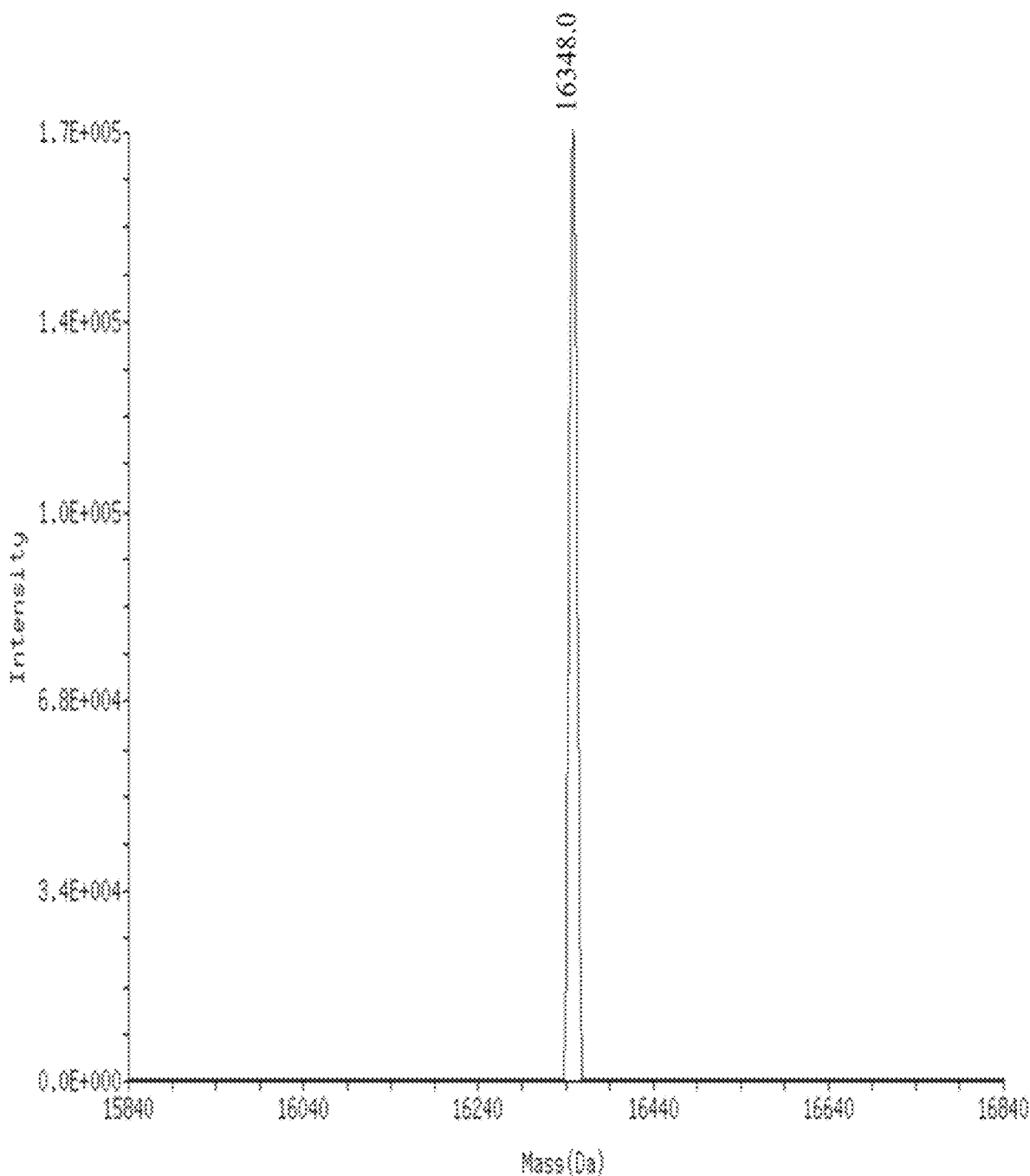
FIG. 5 shows the molecular mass result of antibacterial protein Peocin determined by LC/MS analysis.

Freeze dry the collected supernatant, after resuspending, use adequate amount of digested product to undergo LC-MS examination The results in FIGS. 4,5 showed that the antibacterial protein is identified as starvation/stationary DNA protection protein. The underline marker refers to the matched amino acid, the coverage rate is 36% and the molecular weight is 16.348 kDa, the antibacterial protein is named Peocin.

[Using $E.$ $coli$ Plasmid to Express Antibacterial Protein Peocin]

Construct this functional protein gene fragment on pET-28 plasmid after identified by LC-MS, transform the plasmid to $E.$ $coli$ BL-21 (DE3) (labelled as $E.$ $coli$ BL21 (DE3)/pET-28-peocin), thus the $E.$ $coli$ will express antibacterial protein Peocin. The induction expression steps is described below.

Add 30 µl $E.$ $coli$ BL21 (DE3)/pET-28-peocin bacterial liquid and 3 µl Kanamycin (100 mg/ml) to 3 ml LB culture broth and incubate for 24 hours. After incubation, add 0.5 ml medium and 50 µl Kanamycin (100 mg/ml) in 50 ml LB culture broth, incubate for 3 hours and add 50 µl 1M IPTG to induce expression of high-level production of protein. Incubate for 9 hours, measure the OD$_{600}$ nm absorbance of bacterial broth, concentrate the bacterial liquid to OD600 nm=60/ml, wash with 1×PBS for once, place the bacterial broth in centrifuge and centrifuge it for 15 minutes with the speed of 1300 rpm. Remove the supernatant, add 2 ml 1×PBS and lyse by ultrasonic machine under 5 seconds on/5 seconds off cycle for 5 minutes, then again place the bacterial broth in centrifuge and centrifuge it for 20 minutes under 4° C. with the speed of 4000 rpm. Extract the supernatant and filter it using 0.45 µm syringe filter, then preserve the sample in 4° C. freezer to await for further steps. Load $E.$ $coli$ BL21 (DE3)/pET-28 and $E.$ $coli$ BL21 (DE3)/pET-28-peocin in the same SDS-PAGE to confirm that the transformed plasmid do express antibacterial protein in high-level production, then test antibacterial activity and measure inhibitory zone of $E.$ $coli$ BL21 (DE3)/pET-28 and $E.$ $coli$ BL21 (DE3)/pET-28-peocin protein sample on TSB medium containing $E.$ $coli$ to confirm the antibacterial ability of expressed protein.

Figure 6:
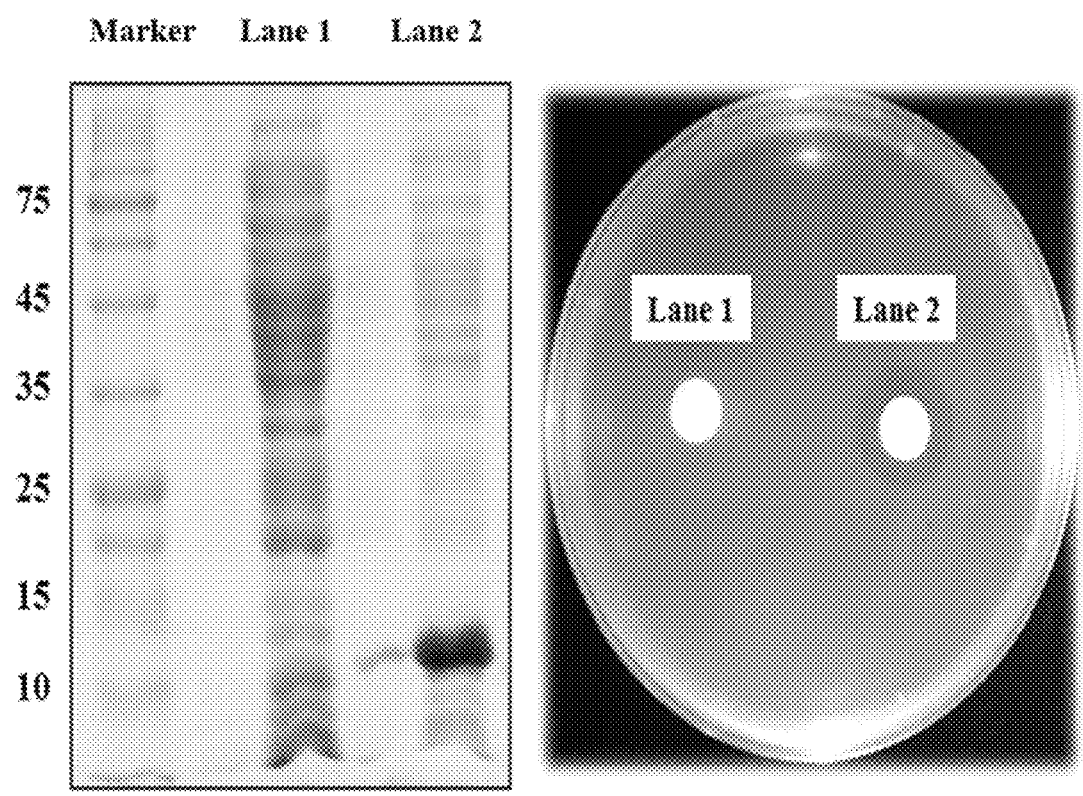
FIG. 6 shows protein electropherogram of antibacterial protein Peocin expression in *E. coli* BL21 (DE3)/pET-28-peocin using SDS-PAGE including comparative antibacterial activity image of cell disrupted supernatant *E. coli* BL21 (DE3) of empty vector pET-28 and cell disrupted supernatant of *E. coli* BL21 (DE3)/pET-28-peocin.

Results showed that after inducing $E.$ $coli$ BL21 (DE3)/pET-28-peocin to express high-level production of antibacterial protein, the growth of $E.$ $coli$ BL21 (DE3)/pET-28-peocin itself was not affected by the induction. However, after *E. coli* BL21 (DE3)/pET-28-peocin is lysed and centrifuged, result of antibacterial activity analysis of supernatant (FIG. 6) showed that the supernatant of lysed pET-28-peocin empty vector (sample 1 in FIG. 6) itself has no bacterial activity; whereas the supernatant of lysed *E. coli* BL21 (DE3)/pET-28-peocin has significant antibacterial effect (sample 2 in FIG. 6). This result showed that the aforementioned starvation/stationary DNA protective protein (peocin) has no antibacterial activity when it is expressed in *E. coli*, however, it has antibacterial effect when released outside of *E. coli*. Moreover, this antibacterial protein can be greatly express via *E. coli* BL21 (DE3)/pET-28-peocin.

[Safety Dosage Determination of NPUST-1 for Fish]

Use zebrafish as experimental model to test whether NPUST-1 is toxic and its safety dosage for the fish. Detailed experimental steps comprising, extract −80° C. NPUST-1 glycerol stock, inoculate 0.5 ml stock culture in 50 ml TSB culture broth, culture in 28° C. for 24 hours. The following day, add 1 ml of the cultured bacterial broth in 100 ml fresh TBS culture broth, culture it in 28° C. for 24 hours, use plating method to calculate number of cell colony, centrifuge the cultured *P. ehimensis* NPUST-1 for 10 minutes with the speed of 12000 rpm to remove the supernatant, then resuspend with 1×PBS buffer, dilute the bacterial liquid to $1\times10^7$, $1\times10^8$, $1\times10^9$, $1\times10^{10}$ and $1\times10^{11}$ CFU/ml respectively. Use 30 G needle to inject 10 µl of diluted culture of each concentration respectively into zebrafish abdominal cavity. Inject 10 zebrafish for each concentration group respectively, then feed the zebrafish of different groups in respective tanks for 2 weeks after injection and observe their health condition and death rate during this period.

Figure 7:
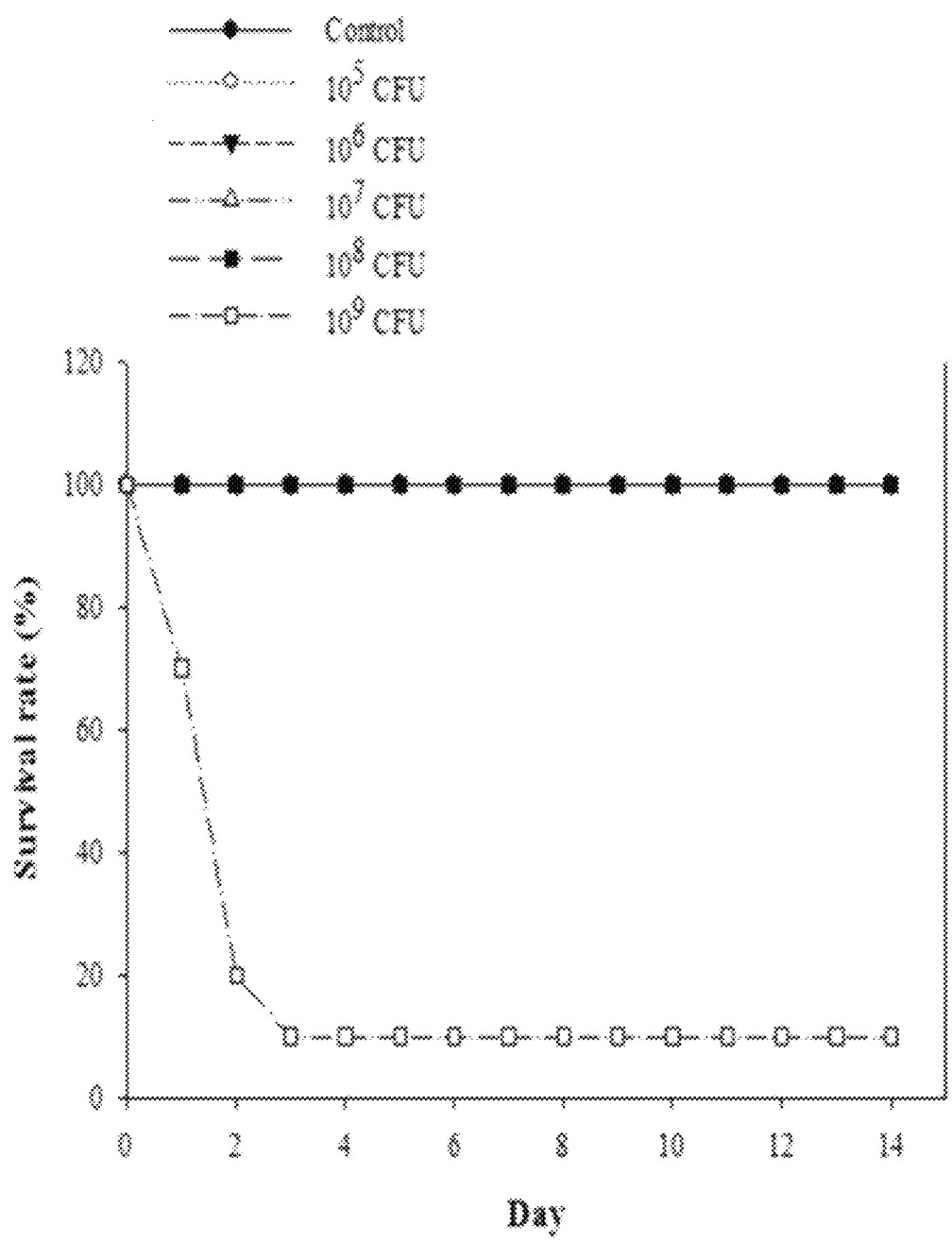
FIG. 7 shows safety concentration test result of zebrafish challenged with different dosage of NPUST-1.

Results showed in FIG. 7 indicated that when the injection concentration is $1\times10^5$, $1\times10^6$, $1\times10^7$, $1\times10^8$ CFU/fish, the survival rate of zebrafish remains 100%. Since injection of high concentration NPUST-1 ($1\times10^8$ CFU/fish) did not cause any fatality to the fish, it is recognized that NPUST-1 is not toxic to the fish. Moreover, $1\times10^6$ or $1\times10^7$ CFU/fish can be the safety dosage for the fish.

To prepare a feed containing NPUST-1 strain, NPUST-1 is cultured in advance and added into mixture on the same day of feed preparation. The additional amount has no specific restriction as long as it is under safety dosage. For example, $1\times10^6$ CFU/g and $1\times10^7$ CFU/g of bacteria can be added into feed for zebrafish and tilapia. Detail steps are mentioned in below.

Ingredients of the feed are shown in table 1 and 2. Add moderate amount of NPUST-1 bacterial broth, fish meal, soybean meal, gluten, corn starch, carboxymethylcellulose, a starch measured by scale and mix it using agitator. After thoroughly agitated, slowly add canola oil containing vitamins and minerals. After fully mixed, add reverse osmotic water slowly and intermittently until the mixed feed appear dough-like, knead the feed dough by hand to check if the moisture is too wet or dry for the subsequent pelleting, after sufficient moisture is confirmed, take the feed dough out of agitator and pick a small piece of feed dough into extruding machine. Extrude feed dough and cut the extruded feed into moderate size by utility knife at the same time, equally spread feed on plate after cutting, place feed under air conditioner for cool air to dry until the feed is dried for certain, then pack the feed in bags and freeze them in 4° C. freezer. Furthermore, use grinder to grind the feed and filter it using 2 different size of sifting screen. One screen has extremely small size of hole for small feeds particles, and the other screen has average hole size for bigger feed particles. The filtered feeds need to be grinded respectively to make appropriate bite-size for zebrafish and tilapia.

TABLE 1

| Ingredients | Protein (%) | Lipid(%) |
| --- | --- | --- |
| Fish meal | 66.1 | 8.63 |
| Soybean meal | 42 | 2 |
| Gluten | 71.2 | 2 |
| Corn starch | 0.18 | 2.65 |

TABLE 2

| Ingredients | Control | $10^6$ CFU/g | $10^7$ CFU/g |
| --- | --- | --- | --- |
| Fish meal | 100 | 100 | 100 |
| Soybean meal | 470 | 470 | 470 |
| Gluten | 180 | 180 | 180 |
| Corn starch | 54 | 54 | 54 |
| Canola oil | 57 | 57 | 57 |
| Carboxymethyl cellulose | 10 | 10 | 10 |
| α starch | 100 | 100 | 100 |
| Vitamin | 10 | 10 | 10 |
| Mineral | 19 | 19 | 19 |
| NPUST-1 (CFU/kg) | 0 | $1\times10^9$ | $1\times10^{10}$ |
| Total(g) | 1000 | 1000 | 1000 |

The feeding of the aforementioned feed containing NPUST-1 bacteria strain, which is fed as a probiotic for organisms, has no specific restrictions. For example, the feeding can follow the treatment mentioned below, which uses NPUST-1 as a probiotic for zebrafish and tilapia.

Feeding of zebrafish: The amount to feed daily is 2% of the fish weight and separated into 2 feeding time.

Feeding of tilapia: Feed twice a day, the amount to feed each time is 5% of fish weight. Measure the fish weight every week after feeding and adjust the feed amount.

EMBODIMENTS

The embodiments below are used for illustrating the objectives and effects of the present invention, which are not to be seen as limitation.

Embodiment 1: Evaluation of Antibacterial Protein Temperature Tolerance

Evaluate the tolerance of purified antibacterial protein Peocin of present invention under different temperature. Evaluation steps are described as below.

Place 100 µl Peocin under 30° C., 40° C., 50° C., 60° C., 70° C., 80° C., 90° C., 100° C. and 121° C. respectively and stand for an hour, all treatment group except 121° C. group is put in the dry bath incubator, which can set to temperature 30° C.~100° C. The 121° C. group is put in the sterilizer which can proceed wet heat sterilize at 121° C. Use Peocin stored under 4° C. as control group, and use the TSB agar plate containing *E. coli* to measure antibacterial activity and inhibitory zone diameter after an hour.

Figure 8:
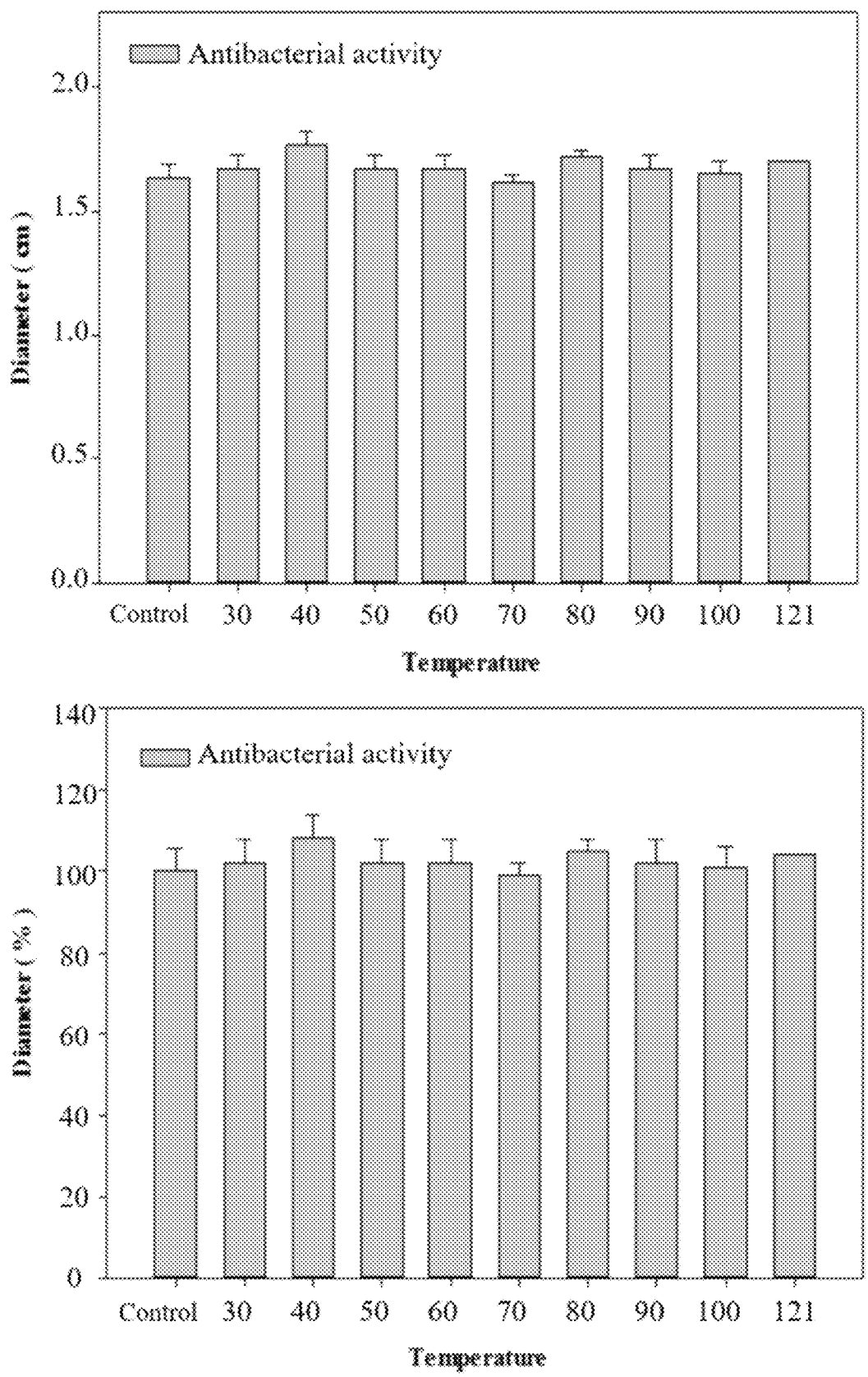
FIG. 8 shows the antibacterial activity of antibacterial protein Peocin under different temperature.

Results showed in FIG. 8 indicated that purified Peocin can still maintain original antibacterial activity after treating under 30° C., 40° C., 50° C., 60° C., 70° C., 80° C., 90° C., 100° C. and 121° C. for 1 hour. Even if the protein is treated under 121° C. for one hour, antibacterial activity is still not destructed, which showed Peocin has great temperature tolerance.

Evaluation of Antibacterial Protein pH Tolerance

Evaluate the tolerance of purified antibacterial protein Peocin of present invention under different pH environment. Evaluation steps are described as below.

Add the purified antibacterial substance in PBS buffer pH7.4 as control group. The experimental groups comprise pH 2, pH3, pH 4, pH 5, pH 6, pH 7, pH 8, pH 9 and pH 10 group, the buffer used for different pH treatment are Glycine-HCl buffer (pH 2.0), Citrate-phosphate McIlvaine buffer (pH 3.0, 4.0, 5.0 and 6.0), Sodium-phosphate buffer (pH 7.0), Tris(hydroxymethyl) aminomethane buffer (pH 8.0 and 9.0) and Glycine-NaOH buffer (pH 10.0). First, add 500 μl of purified antibacterial protein in 15 ml centrifuge individually for each group, then add 2 ml of different pH buffer to change pH environment of treated antibacterial substance and stand for 4 hours under 28° C. After 4 hours, measure the antibacterial activity and inhibitory zone diameter using TSB agar plate containing E. coli.

Figure 9:
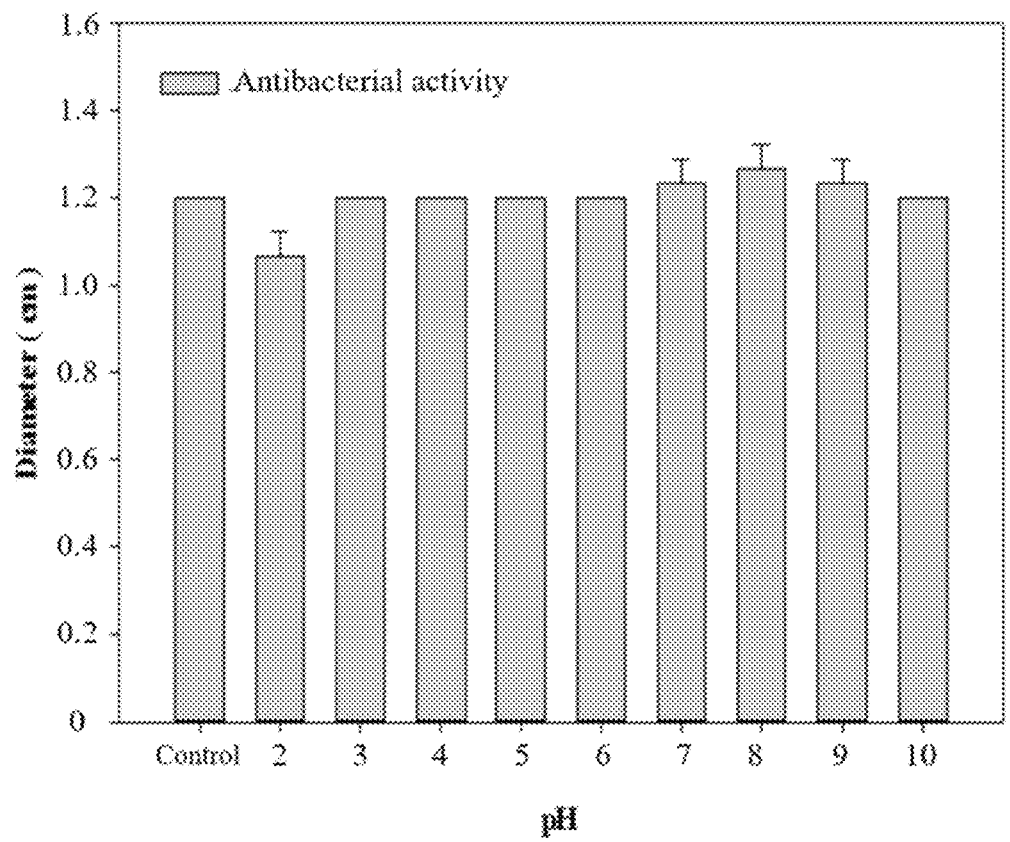
FIG. 9 shows the antibacterial activity of antibacterial protein Peocin under different pH condition.
Figure 9:
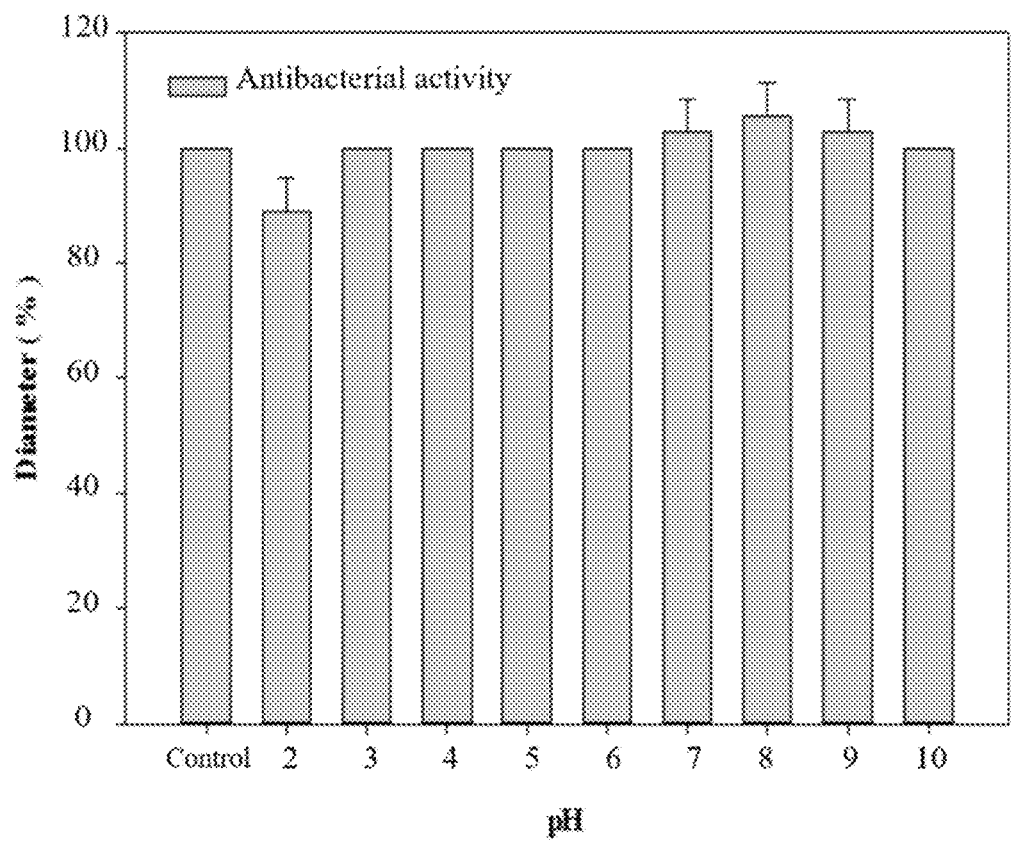

Results showed in FIG. 9 indicated that antibacterial activity of purified Peocin remain stable after treated under different pH 3~10 environment for 4 hours. Even under highly acidic pH2 environment, the 87% of antibacterial activity still remained, which demonstrated that Peocin has great pH tolerance.

[Evaluation of Sensitivity of Antibacterial Protein Peocin to Protease]

Evaluate the protease sensitivity of purified antibacterial protein. Detailed steps are described below.

Figure 10:
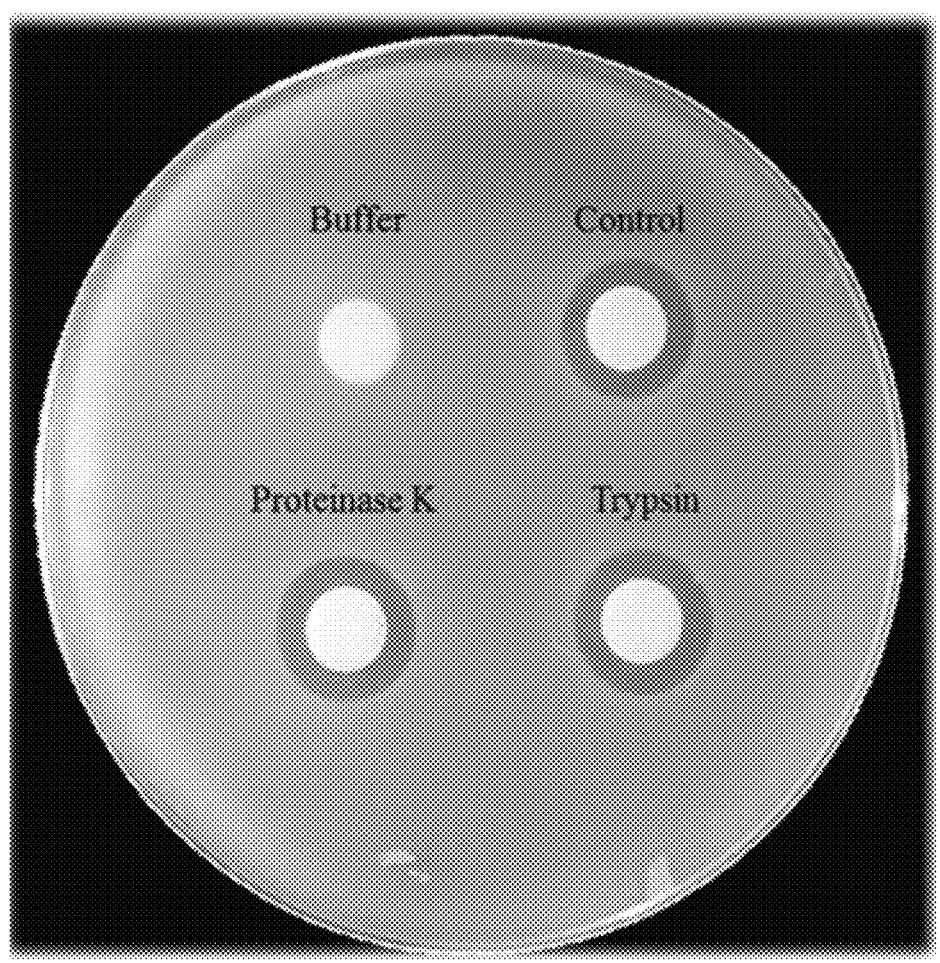
FIG. 10 shows the antibacterial activity stability of antibacterial protein Peocin after treating with protease K and trypsin.

Evaluate sensitivity of Peocin to proteinase K and trypsin respectively. First, add 180 μl of purified antibacterial protein peocin into 1.7 ml micro-centrifuge tube, then add 20 μl of 10 mg/ml proteinase K and trypsin respectively for the final concentration of protease to be 1 mg/ml, then stand for 4 hours under 37° C. for reaction. Next, use TSB agar plate containing E. coli to measure the antibacterial activity and inhibitory zone diameter. For comparison, use PBS buffer without antibacterial protein as buffer group, and control group is purified antibacterial protein peocin without protease. Results showed in FIG. 10 indicated that purified Peocin treated with protease K and trypsin for 4 hours still expressed stable antibacterial activity. According to this result, it can be recognized that Peocin will not be hydrolyzed by Protease K and trypsin, which means it has low sensitivity to protease and is adapted for preservation for industrial purposes.

[Evaluation of Antibacterial Protein Stability Under Different Temperature]

Evaluate the stability of purified antibacterial protein of present invention under different temperature. Detailed steps are described below.

Place purified antibacterial protein Peocin sample in 40° C., room temperature, 4° C. and −20° C. environment respectively for 70 days. Each week during the experiment, extract samples and measure their antibacterial activity and inhibitory zone diameter using TSB agar plate containing E. coli.

Figure 11:
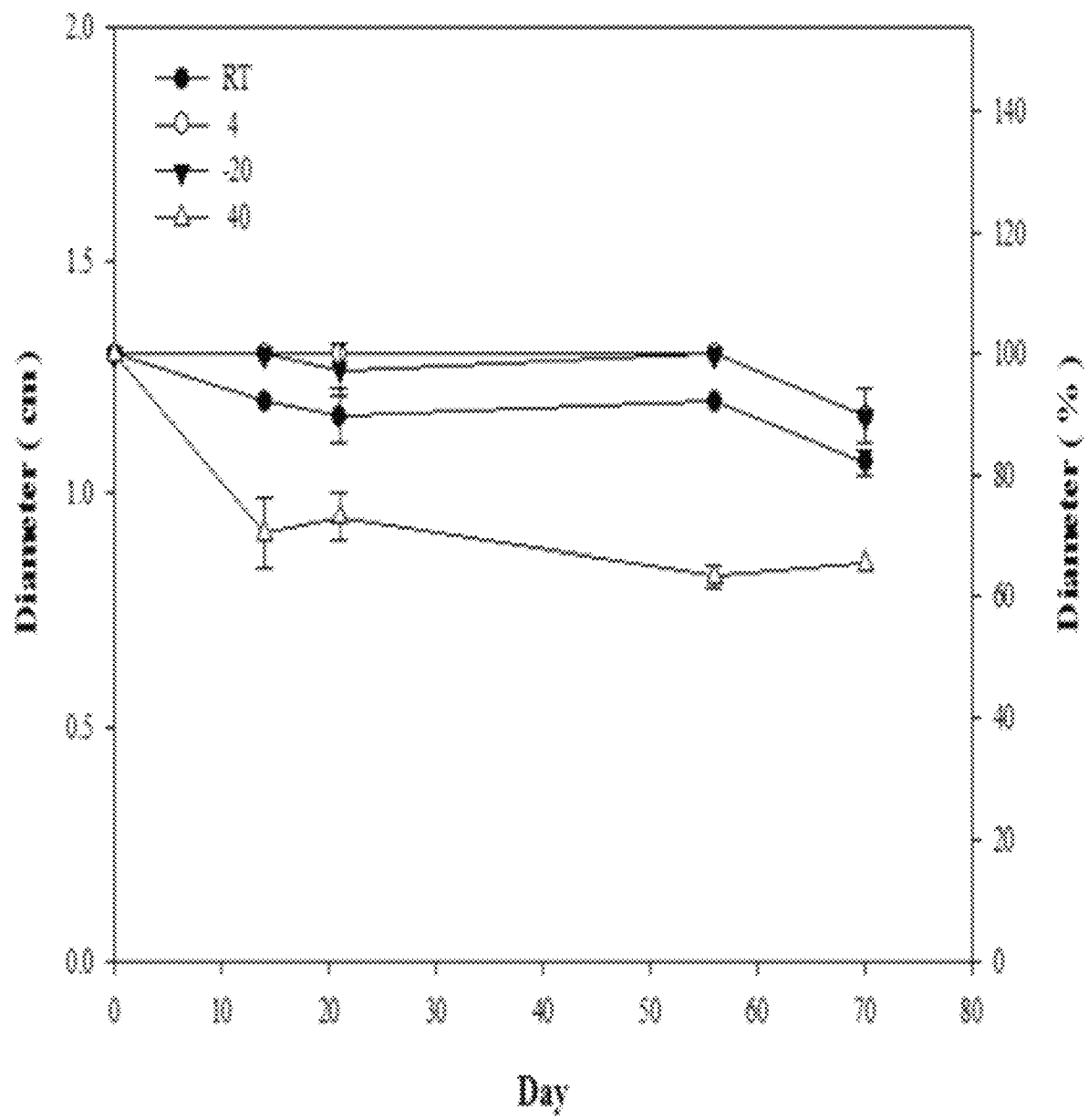
FIG. 11 shows the antibacterial activity of antibacterial protein peocin under different preservation temperatures for 70 days.
Figure 12:
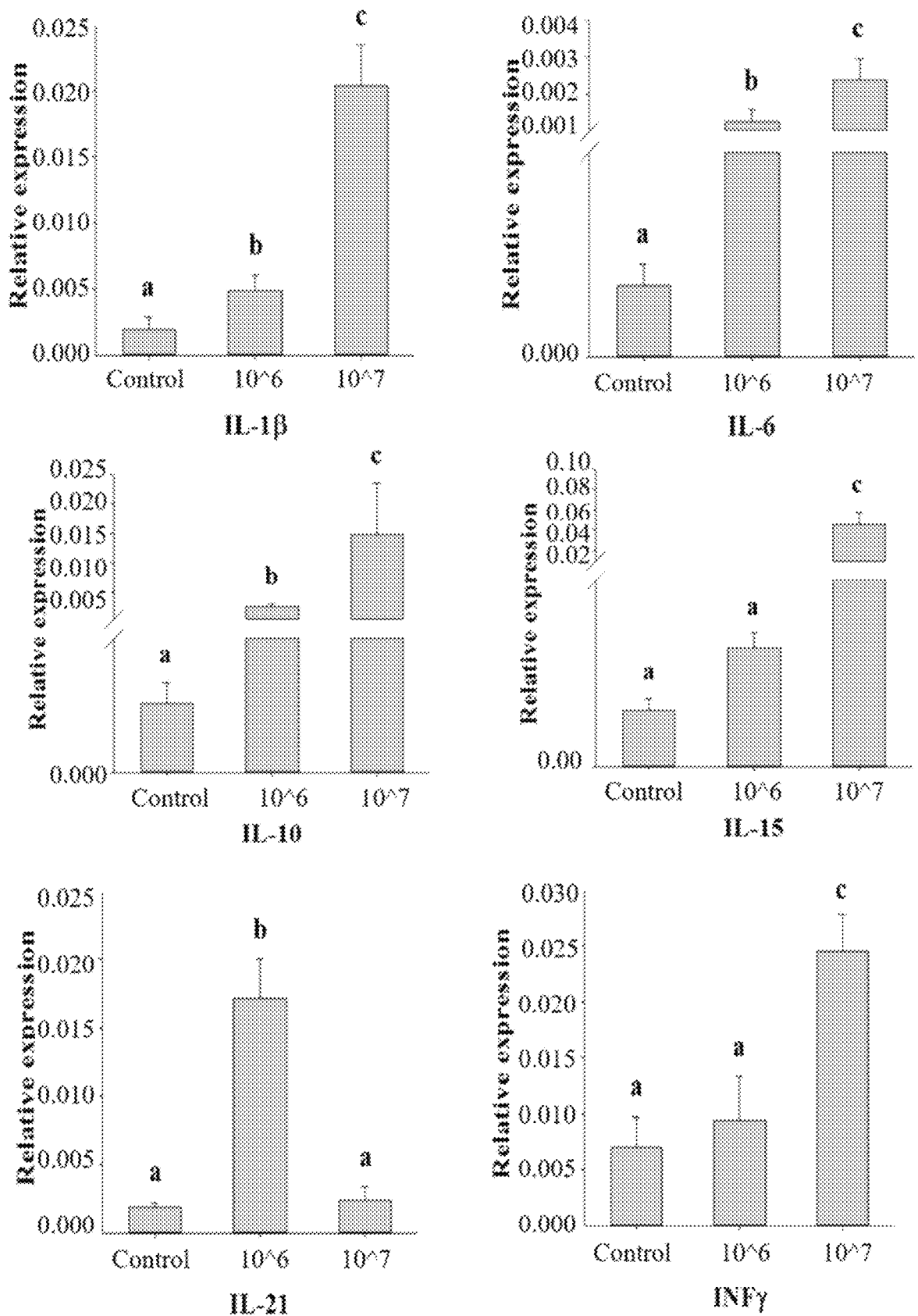
FIG. 12 shows comparative expression of the immune genes in intestinal of zebrafish fed with feed containing NPUST-1.
Figure 13:
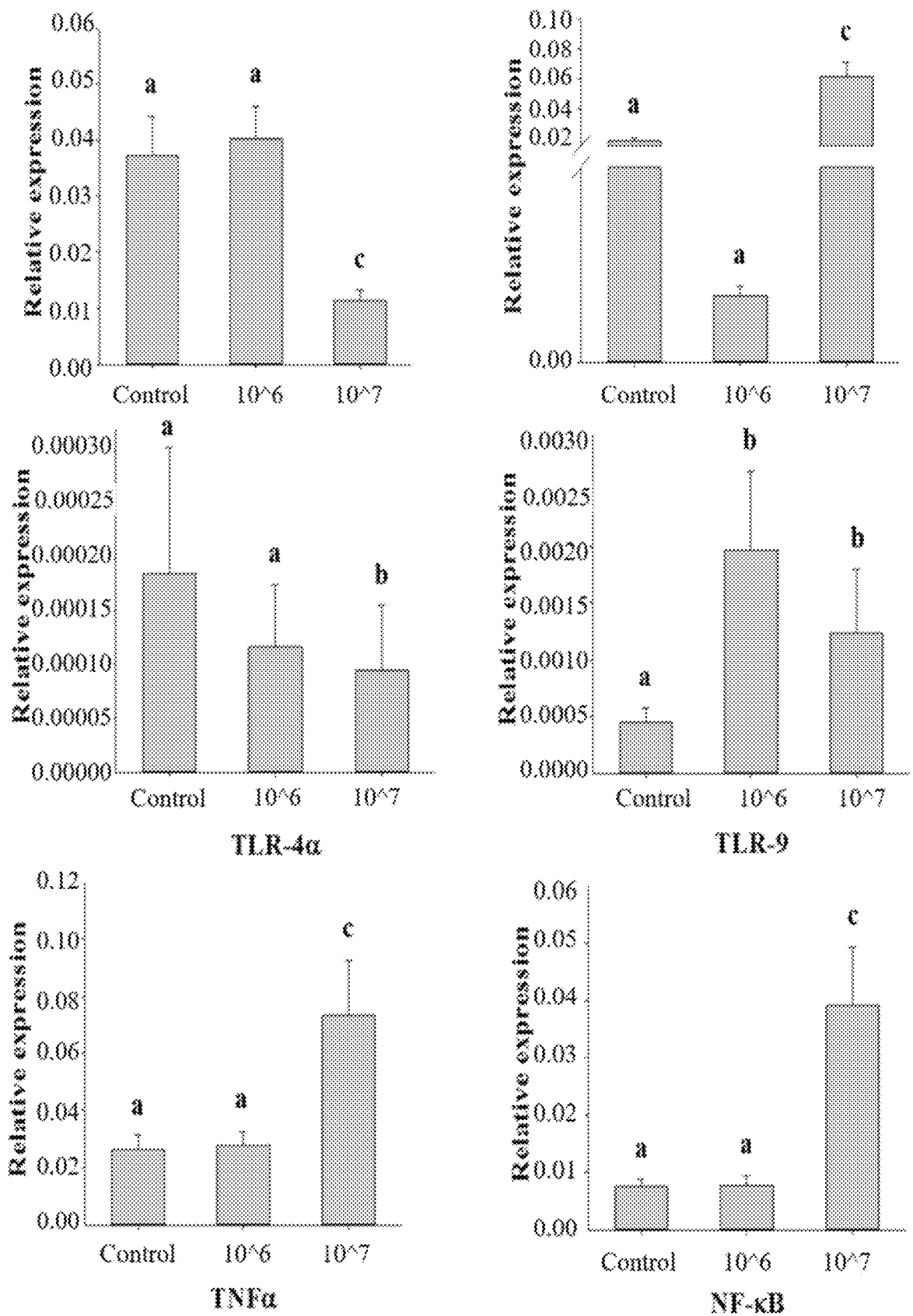
FIG. 13 shows comparative expression of the immune genes in intestinal of zebrafish fed with feed containing NPUST-1.
Figure 14:
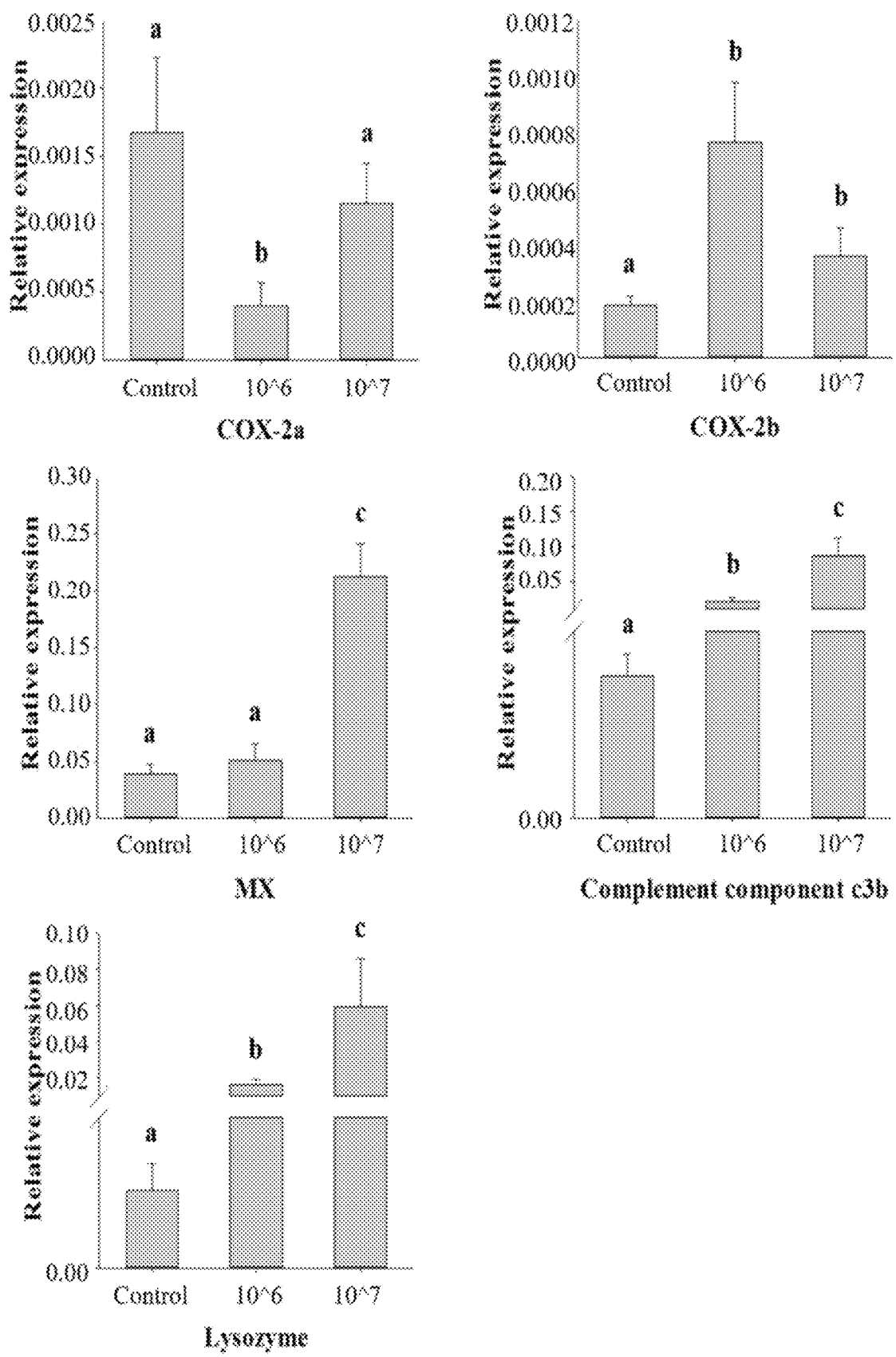
FIG. 14 shows comparative expression of the immune genes in intestinal of zebrafish fed with feed containing NPUST-1.
Figure 15:
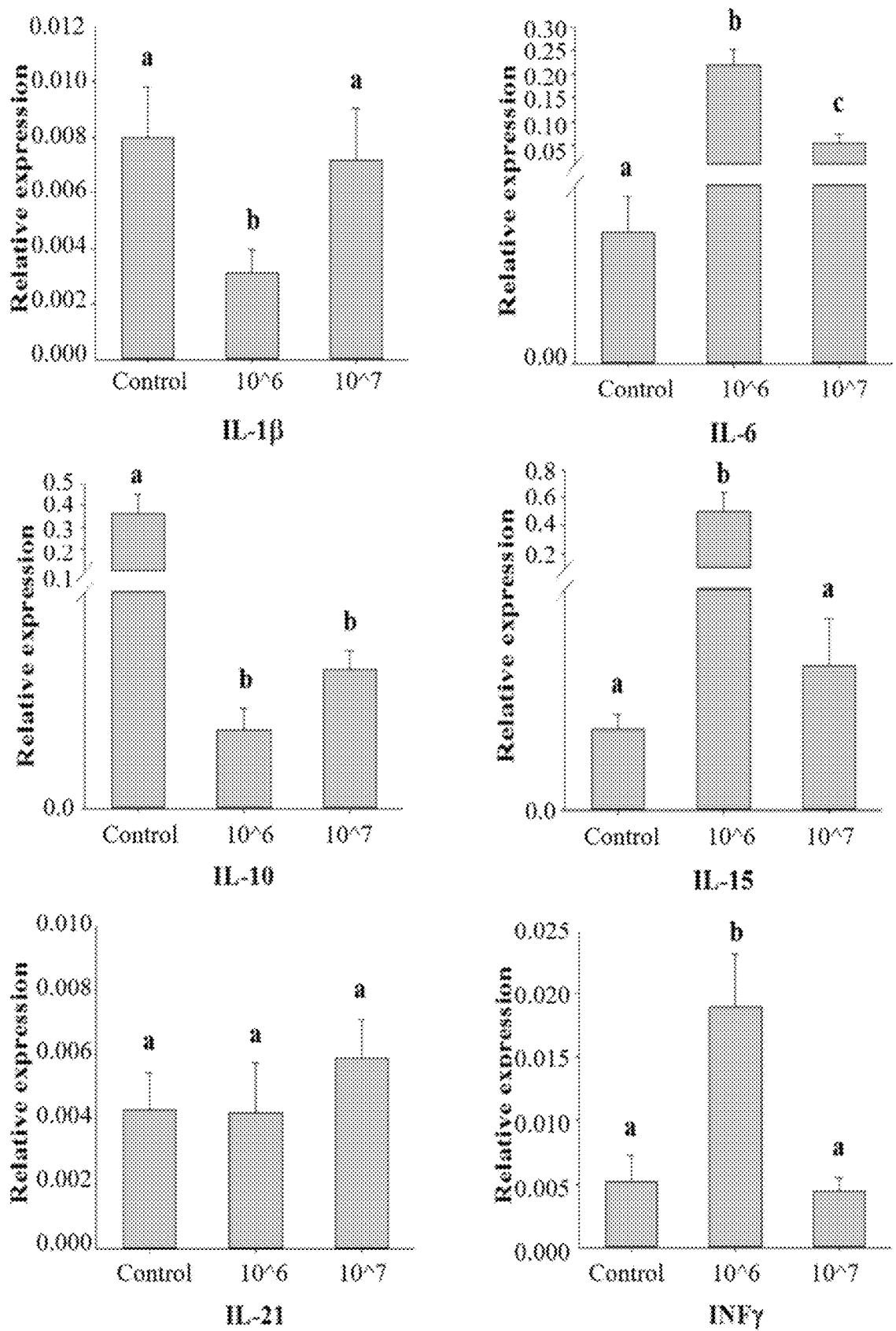
FIG. 15 shows comparative expression of the immune genes in whole body of zebrafish fed with feed containing NPUST-1.
Figure 16:
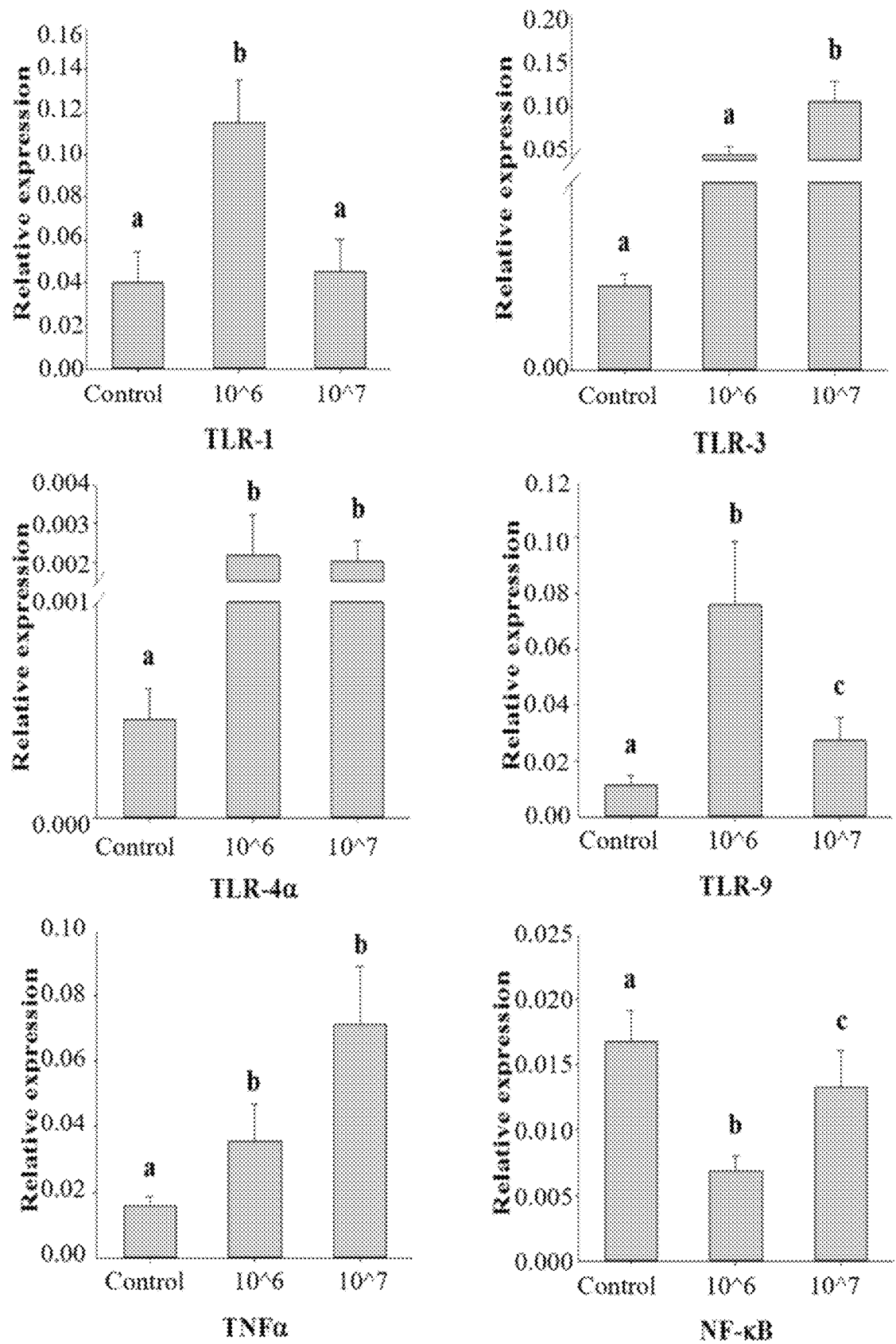
FIG. 16 shows comparative expression of the immune genes in whole body of zebrafish fed with feed containing NPUST-1.
Figure 17:
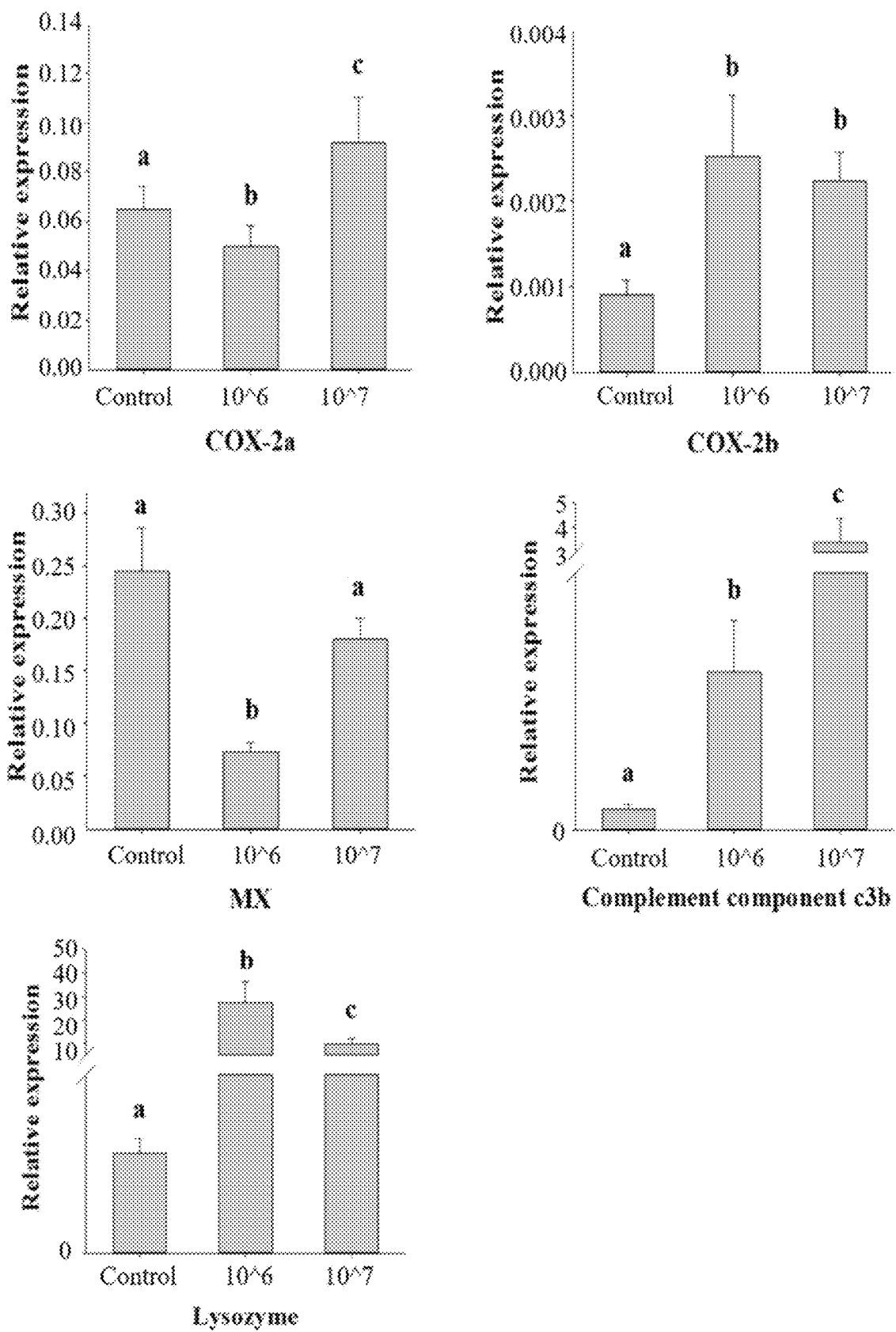
FIG. 17 shows comparative expression of the immune genes in whole body of zebrafish fed with feed containing NPUST-1.

Results showed in FIG. 11 indicated that purified Peocin preserved under −20° C. and 4° C. environment for 70 days still remained 90% antibacterial activity; those preserved under room temperature for 70 days still remained 80% antibacterial activity; those preserved under 40° C. for 70 days still remained 66% antibacterial activity. From this result it can be recognized that Peocin can still maintain active stability after preserved under −20° C. and 4° C. environment for a long period and is adapted for preservation for industrial purposes.

[Evaluation of Antibacterial Effect of Antibacterial Protein Peocin Against Various Pathogens]

Evaluate the antibacterial effect of purified antibacterial protein Peocin of present invention against various aquaculture pathogens and foodborne pathogens.

Following pathogens were subjected in the test. Six aquaculture pathogen: Aeromonas hydrophila, Vibrio vulnificus, Vibrio alginolyticus, Vibrio parahaemolyticus, Streptococcus agalactiae and Debaryomyces hansenii. Five foodborne pathogen which cause food rot and food poisoning: Staphylococcus aureus, Methicillin-resistant Staphylococcus aureus (MRSA), Escherichia coli, Salmonella typhimurium and Listeria monocytogenes. Two clinical infectious pathogens: Pseudomonas aeruginosa and Burkholderia gladioli causing leaf spot disease. Culture these strains separately and create solid medium containing these strains ($10^6$ CFU/ml). Add antibacterial protein after solid medium solidifies, then measure the antibacterial activity and inhibitory zone diameter.

Results showed in table 3 indicated that Peocin has antibacterial effect against all of aforementioned pathogens from different sources. In particular, better inhibition effect is shown against B. gladioli, S. agalactiae and E. coli. Thus it can be seen, the antibacterial effect of Peocin is broad-spectrum and has potential applying in diseases caused by different pathogens.

TABLE 3

| Pathogen | Diameter of inhibitory zone(cm) |
|---|---|
| Aeromonas hydrophila | 1.3 ± 0.00 |
| Streptococcus agalactiae | 1.4 ± 0.00 |
| Vibrio vulnificus | 1.3 ± 0.00 |
| Vibrio alginolyticus | 1.1 ± 0.03 |
| Vibrio parahaemolyticus | 1.2 ± 0.03 |
| Debaryomyces hansenii | 1.3 ± 0.00 |
| Escherichia coil | 1.4 ± 0.00 |
| Staphylococcus aureus | 1.1 ± 0.05 |
| Methicillin-resistant Staphylococcus aureus | 1.1 ± 0.05 |
| Salmonella typhimurium | 1.1 ± 0.05 |
| Listeria monocytogenes | 1.0 ± 0.05 |
| Pseudomonas aeruginosa | 1.2 ± 0.00 |
| Burkholderia gladioli | 1.5 ± 0.05 |

To find out competent antibiotics for combination with NPUST-1 bacterial strain used as a probiotic, inhibition effect of varies aquacultural antibiotics against NPUST-1 bacterial strain are examined. Detailed testing steps are described as below.

Following antibiotics are examined: amoxicillin, ampicillin, doxycycline, erythromycin, furazolidone, flumequine, ormetoprim, oxytetracycline, sulfadimethoxine, chloramphenicol, gentamycin and kanamycin. The antibiotics concentration (shown in table 4) being tested are the available maximum concentration conformed to the drug regulation for aquaculture. After all the antibiotics are prepared, use TSB agar plate containing P. ehimensis NPUST-1 to determine the antibacterial activity and measure the inhibitory zone of antibiotics.

Results in table 4 showed that only Ampicillinm and Sulfadimethoxine have no inhibition effect against P. ehimensis NPUST-1, while other testing drugs have inhibition effect against P. ehimensis-NPUST-1 and generate different size of inhibitory zone on plate. Therefore, although NPUST-1 has no drug resistance against most antibiotics, it is resistant to Ampicillinm and Sulfadimethoxine. Thus these antibiotics can be used during the biological control in aquaculture but cause no reduction to the said effect of NPUST-1.

TABLE 4

| Antibiotic | Use concentration | Final concentration | inhibitory zone size |
|---|---|---|---|
| Amoxicillin | 40 μg/g | 40 μg | 2.30 ± 0.10 |
| Ampiciliin | 20 μg/g | 20 μg | — |
| Doxycycline | 50 μg/g | 50 μg | 3.30 ± 0.00 |
| Erythromycin | 50 μg/g | 50 μg | 1.73 ± 0.06 |
| Furazolidone | 2 μg/g | 2 μg | 1.00 ± 0.00 |
| Flumequine | 20 μg/g | 20 μg | 5.67 ± 0.06 |
| Ormetoprim | 50 μg/g | 50 μg | 4.60 ± 0.00 |
| Oxytetracycline | 50 μg/g | 50 μg | 2.13 ± 0.06 |
| Sulfadimethoxine | 100 μg/g | 100 μg | — |
| Chloramphenicol | 80 ppm | 80 ppm | 2.67 ± 0.06 |
| Gentamycin | 4 ppm | 4 ppm | 2.03 ± 2.03 |
| Kanamycin | 100 ppm | 100 ppm | 1.13 ± 0.03 |

[Promotion of Zebrafish Immune Genes Expression Via NPUST-1]

Using zebrafish as subject to evaluate the efficacy of NPUST-1 as probiotics in immune genes expression promotion. Detailed steps are described below.

Zebrafish AB strain from Taiwan Zebrafish Core Facility at Academia Sinica is used in the evaluation. For each group, 15 zebrafish were raised in 20 L independent tank with average weight 0.61±0.04 g. Groups of feeding experiment consist of: 3 tanks as control groups, 3 tanks as group fed with $1 \times 10^6$ CFU/g NPUST-1 and 3 tanks as group fed with $1 \times 10^7$ CFU/g NPUST-1. Daily feed intake for the fish is 2% of the fish weight, and feed was fed apart in two separate feeding time. Use a siphon to clean the fish tank daily, change the cotton regularly and monitor the lighting period (14 hours light/10 hours dark). After a month of feeding, proceed the following immune gene expression level analysis.

The tissue analysed are is intestinal tract and whole body of zebrafish, remove the intestine from fish and soak it in 2 ml micro centrifuge tube containing 1 ml TriPure to extract tissue RNA, use anatomic scissors to cut up rest of the body and transfer them into 15 ml centrifuge tube containing 4 ml TriPure to extract tissue RNA. Place the tissue in TriPure and homogenize it with homogenizer, afterwards, add 200 μl Chloroform and shake gently for 30 seconds, then place on ice for 5 minutes. Wait until tissue fragments precipitated, then stratify the sample by centrifuging it for 15 minutes under 4° C. with the speed of 12000 rpm. After centrifugation, transfer the clear supernatant into a new 1.7 ml micro centrifuge tube. Add 500 μl Isopropanol and mix, stand for 10 minutes in room temperature for RNA precipitation. After 10 minutes, centrifuge the mixture under 4° C. with the speed of 12000 rpm for 10 minutes to deposit the RNA to the bottom of the micro centrifuge tube. Afterwards, remove the supernatant and wash the pellet with 75% ethanol, centrifuge the pellet for 10 minutes at the speed of 12000 rpm to remove most ethanol, place on table for ethanol to fully evaporate, then add 20 μl water containing 0.1% DEPC to dissolve RNA. Thereafter, determine the RNA concentration using ultramicro-spectrophotometer, then use Bio-Rad IscriptTMcDNA Synthesis kit to generate cDNA from RNA. Preserve the cDNA in −20° C. Afterwards, use the primer of each gene listed in table 5 to undergo real-time PCR to determine immune gene expression level.

TABLE 5

| Immune gene | Primer sequence (5'-3') | Ref. sequence | SEQ ID NO. |
|---|---|---|---|
| Interleukin-1β (IL-1β) | TGGACTTCGCAGCACAAAATG | AY340959 | 2 |
| | CACTTCACGCTCTTGGATGA | | 3 |
| Interleukin-6 (IL-6) | TCAACTTCTCCAGCGTGATG | JN698962 | 4 |
| | TCTTTCCCTCTTTTCCTCCTG | | 5 |
| Interleukin-10 (IL-10) | TCACGTCATGAACGAGATCC | BC163031 | 6 |
| | CCTCTTGCATTTCACCATATCC | | 7 |
| Interleukin-15 (IL-15) | ATGTCATTGGAACTCAGAG-GTTTG | BC162843 | 8 |
| | CTGTTCTGGATGTCCTGCTTGA | | 9 |
| Interleukin-21 (IL-21) | AATCATTCATCGTGGACAGT-GTGT | NM_001128574 | 10 |
| | AACGTTCGGCTGTTGACCAT | | 11 |
| Tumor necrosis factor-α (TNF-α) | AAGGAGAGTTGCCTTTACCG | BC165066 | 12 |
| | ATTGCCCTGGGTCTTATGG | | 13 |
| Interferon-gamma (IFN-γ) | GAGAGGCTGGCACATGTTCA | AB126869 | 14 |
| | CCCATAGCGTTTCTGCATACG | | 15 |
| Nuclear factor-kB (NF-kB) | AAGAGGACCAAAATAAGCACAG | AY163838 | 16 |
| | AAGTCCAAGGTACATCGCCATGA | | 17 |
| Cyclooxygenase-2α (COX-2α) | GATCTCCCAAATGCCAAGAC | NM_153657 | 18 |
| | GGGCGAAGAAAGCAAACATG | | 19 |
| Cyclooxygenase-2β (COX-2β) | GAGCTGCCAGACGTGAAGATG | NM_001025504 | 20 |
| | GGGCGAAGAAAGCGAACATA | | 21 |
| Complement component c3b | CGTCTCCGTACACCATCCATT | NM_131243 | 22 |
| | GGCGTCTCATCAGGATTTGTTAC | | 23 |

TABLE 5-continued

| Immune gene | Primer sequence (5'-3') | Ref. sequence | SEQ ID NO. |
|---|---|---|---|
| Lysozyme | CGTGGATGTCCTCGTGTGAAG<br>CCAATGGAGAATCCCTCAAA | NM_139180 | 24<br>25 |
| Toll-like receptor-1 (TLR-1) | CAGAGCGAATGGTGCCACTAT<br>GTGGCAGAGGCTCCAGAAGA | AY38444 | 26<br>27 |
| Toll-like receptor-3 (TLR-3) | TGGAGCATCACAGGGATAAAGA<br>TGATGCCCATGCCTGTAAGA | AY616582 | 28<br>29 |
| Toll-like receptor-4α (TLR-4α) | TGCCTGGTGTCGCTTTGA<br>CCTCTCCGCAACATCTTCCA | EU551724 | 30<br>31 |
| Toll-like receptor-9 (TLR-9) | CGGACACCCAGTATGATGCA<br>CCCCGGTTCTCCAATCTCA | NM_001130594 | 32<br>33 |
| MX | GAGTTTCGACCTTGGCACAGAGA<br>CTGGTCAGCTAGACGCTTGCT | AF533769 | 34<br>35 |
| Elongation factor 1α (EF-1α) | AACAGCTGATCGTTGGAGTCAA<br>TTGATGTATGCGCTGACTTCCT | AY422992 | 36<br>37 |

Results in FIGS. 12, 13, 14, 15, 16, 17 and table 5 showed that expression levels of Interleukin (IL)-1β, IL-6, 11-10, Cyclooxygenase (COX)-2b, Toll-like receptor (TLR)-9, complement C3b and lysosome are significantly elevated in zebrafish intestine tissue; while expression levels of IL-6, Tumor necrosis factor (TNF)-α, COX-2b, TLR-4, TLR-9, complement C3b and lysosome expression levels are significantly elevated in whole body of zebrafish. Therefore, by being fed to zebrafish as probiotics, NPUST-1 showed efficacy of elevating immune gene expression level.

[Elevation of Survival Rate of Pathogen Infected Zebrafish Via NPUST-1]

By infecting zebrafish with *Aeromonas hydrophila*, the experiment examine whether survival rate of infected zebrafish is elevated after being fed with NPUST-1 as probiotics. Detailed steps are described below.

This experiment involved four zebrafish groups: blank group, control group, experimental group 1 and experimental group 2. The experimental group 1 are zebrafish fed with feed containing $1 \times 10^6$ CFU/g NPUST-1, and the experimental group 2 are zebrafish fed with feed containing $1 \times 10^7$ CFU/g NPUST-1. Every group has three tanks applying external filter, and each tank raises 15 zebrafish. Execute the infection after one month of feeding. Use 30G needle to inject 10 µl pathogen sample to zebrafish abdominal cavity. For pathogen sample of each groups, blank group is injected with PBS, control and experimental groups are injected with $1 \times 10^6$ CFU/ml *Aeromonas hydrophila*. Afterward, raise and observe the fish for one week and then record the death rate.

Figure 18:
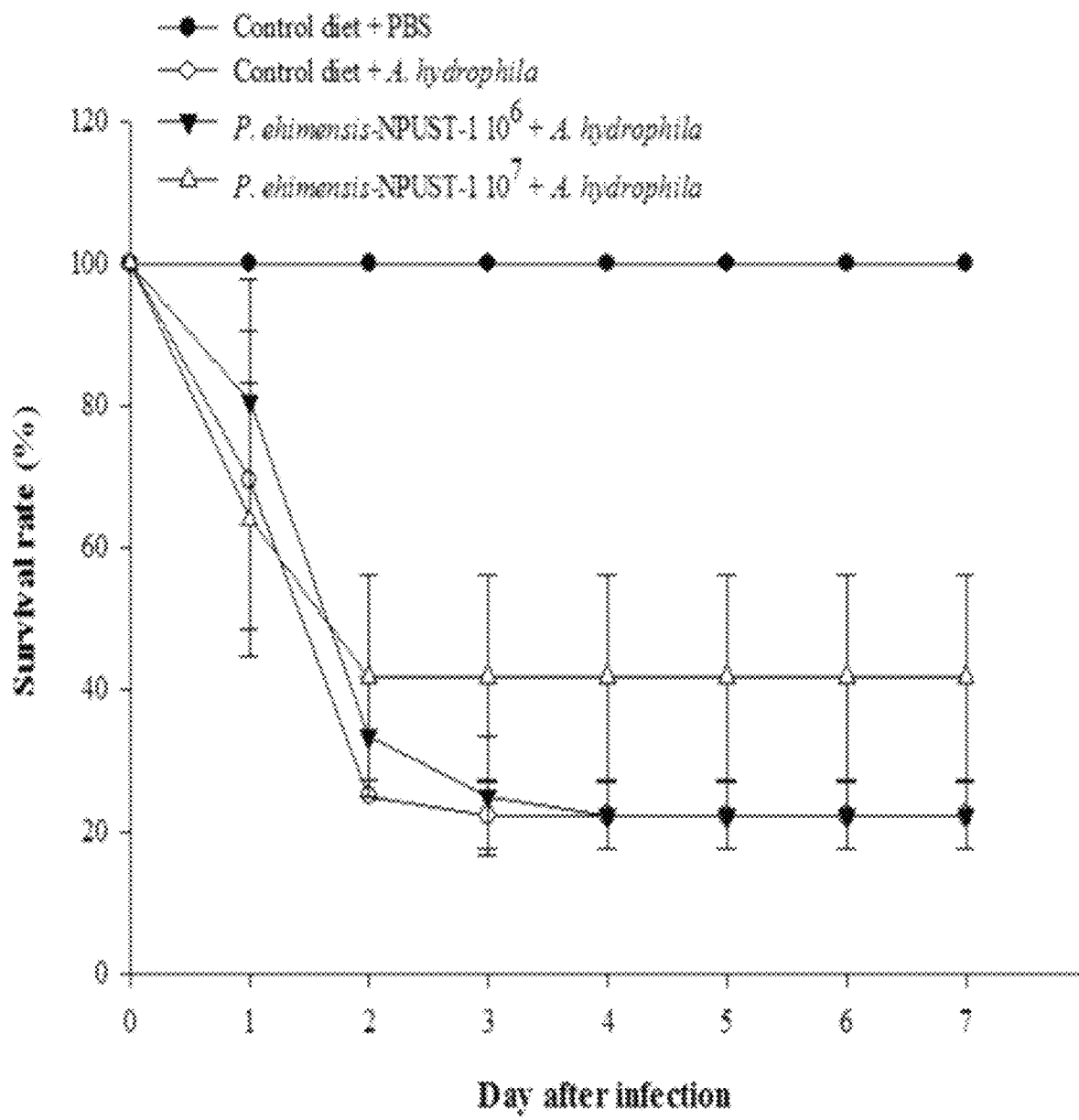
FIG. 18 shows the comparative survival rate of zebrafish treated with feed containing NPUST-1 after infected with *A. hydrophila*.

Results showed in FIG. 18 indicated that the survival rate of PBS injected blank group is 100%, whereas control group showed 22.2%, experimental group 1 fed with $10^6$ CFU/g showed 30.5% and experiment group 2 fed with $10^7$ CFU/g showed 44.4%. It is discovered that fish fed with $10^7$ CFU/g NPUST-1 had a 20% increase in survival rate. Thus it can be seen, by being fed to zebrafish as probiotics, NPUST-1 showed efficacy of elevating survival rate of pathogen infected fish.

[Promotion of Tilapia Immune Gene Expression Level Via NPUST-1]

Using tilapia as subject to evaluate the efficacy of NPUST-1 as probiotics in immune genes expression promotion. Detailed steps are described below.

The tilapia of present experiment is obtained from Dr. Hong-Yi Gong's lab (National Taiwan Ocean University, Department of Aquaculture). Raise the tilapia in 10 L tank, each tank accommodates 20 fish with average fish weight 0.27±0.02 g. The groups of experiment comprise 3 control group, 3 groups fed with $1 \times 10^6$ CFU/g NPUST-1 feeds and 3 groups fed with $1 \times 10^7$ CFU/g NPUST-1 feeds. Feed twice a day with the feed amount being 5% of the fish weight. Measure the fish weight weekly from the beginning of experiment and adjust the feed amount accordingly. After feeding for 2 month, proceed the following immune gene expression level analysis.

This tissue analysed are head kidney and intestines of tilapia. After feeding tilapia for 2 months, take out the head kidney and intestines, soak them in 2 ml micro centrifuge containing 1 ml TriPure to extract tissue RNA. Place the tissue in TriPure and homogenize it with homogenizer, afterwards, add 200 µl Chloroform and shake gently for 30 seconds, then place on ice for 5 minutes. Wait until tissue fragments precipitated, then stratify the sample by centrifuging it for 15 minutes under 4° C. with the speed of 12000 rpm. After centrifugation, transfer the clear supernatant into a new 1.7 ml micro centrifuge tube. Add 500µl Isopropanol and mix, stand for 10 minutes in room temperature for RNA precipitation. After 10 minutes, centrifuge it under 4° C. with the speed of 12000 rpm for 10 minutes to deposit the RNA to bottom of the micro centrifuge tube. Afterwards, remove the supernatant and wash with 75% ethanol, centrifuge the pellet for 10 minutes at the speed of 12000 rpm to remove most ethanol, place on table for ethanol to fully evaporate, then add 20 µl water containing 0.1% DEPC to dissolve RNA. Thereafter, determine the RNA concentration using ultramicro-spectrophotometer, then, use Bio-Rad IscriptTMcDNA Synthesis kit to generate cDNA from RNA. Preserve the cDNA in −20° C. Afterwards, use the primer of each gene listed in table 6 to undergo real-time PCR to determine expression level of immune gene TNF-α and TGF-β (Transforming growth factor beta).

TABLE 6

| Immune gene | Primer sequence (5'-3') | Ref. sequence | SEQ ID NO: |
|---|---|---|---|
| Tumor necrosis factor-α (TNF-α) | CCAGAAGCACTAAAGGCGAAGA CCTTGGCTTTGCTGCTGATC | AY428948A | 38 39 |
| Transforming growth factor-β (TGF-β) | GTTTGAACTTCGGCGGTACTG TCCTGCTCATAGTCCCAGAGA | XM_003459454.2 | 40 41 |

Figure 19:
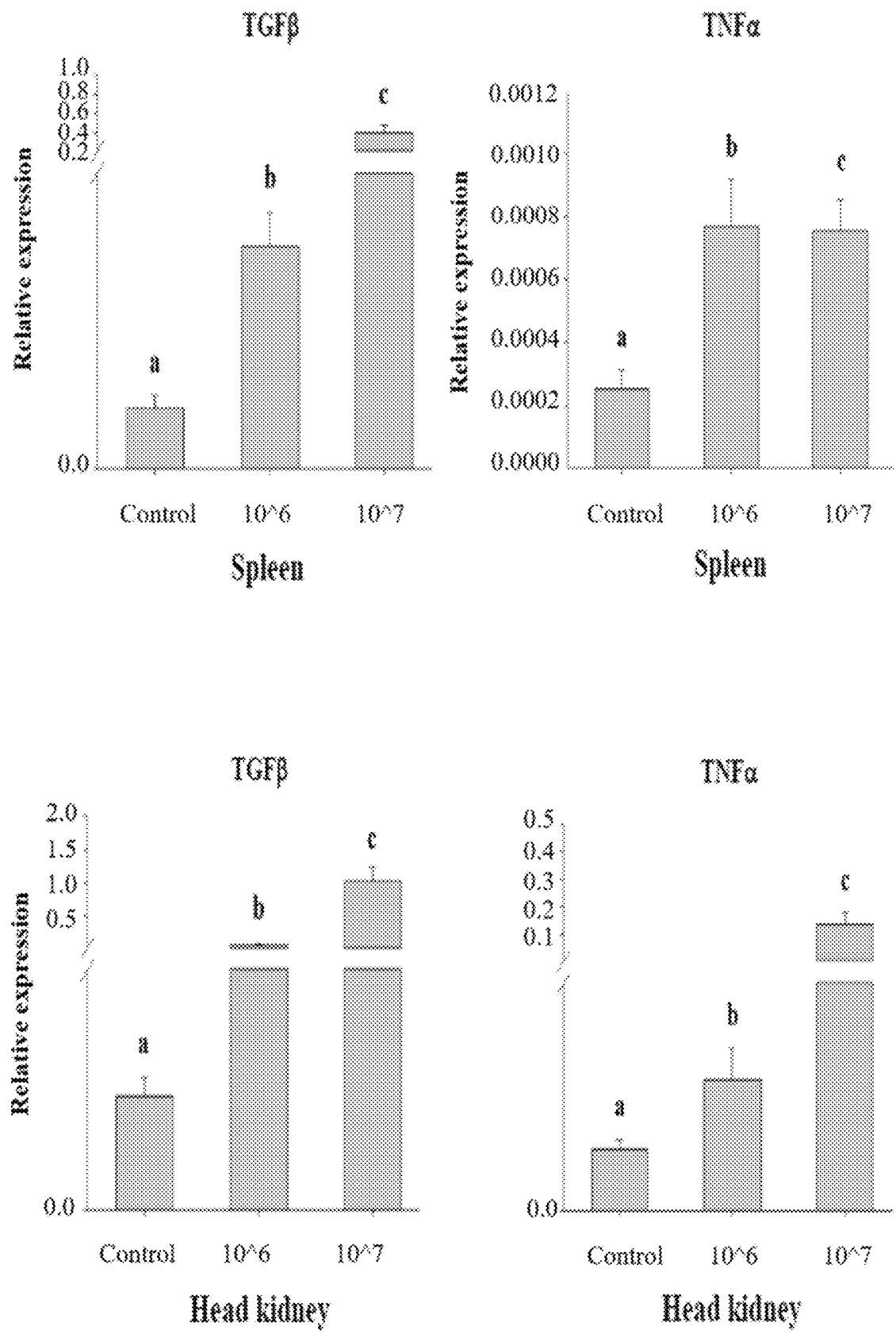
FIG. 19 shows the comparative expression of the immune genes TNF-α and TGF-β in spleen and head kidney of tilapia treated with feed containing NPUST-1.

Results showed in FIG. 19 and table 6 indicated that expression level of TNF-α and TGF-β significantly increased in tilapia spleen and head kidney. Therefore, by being fed to tilapia as probiotics, NPUST-1 showed efficacy of elevating immune gene expression level.

[Elevation of Survival Rate of Pathogen Infected Tilapia Via NPUST-1]

By infecting tilapia with *Aeromonas hydrophila*, the experiment examine whether survival rate of Infected tilapia is elevated after being fed with NPUST-1 as probiotics. Detailed steps are described below.

This experiment involved four tilapia groups: blank group, control group, experimental group 1 and experimental group 2. The experimental group 1 are tilapia fed with feed containing $1\times10^6$ CFU/g NPUST-1, the experimental group 2 are tilapia fed with feed containing $1\times10^7$ CFU/g NPUST-1. The control group are fed with feed without NPUST-1. Every group has three tanks applying recirculating aquaculture system, and each tank raises 15 tilapia. Execute the infection after 1 month of feeding. Use 30G needle to inject 20 μl pathogen sample to tilapia cloaca. For pathogen of each group, blank group is injected with PBS, control and experimental group are injected with $4\times10^7$ CFU/ml *Aeromonas hydrophila*. Afterward, raise and observe the fish for one week and record the death rate.

Figure 20:
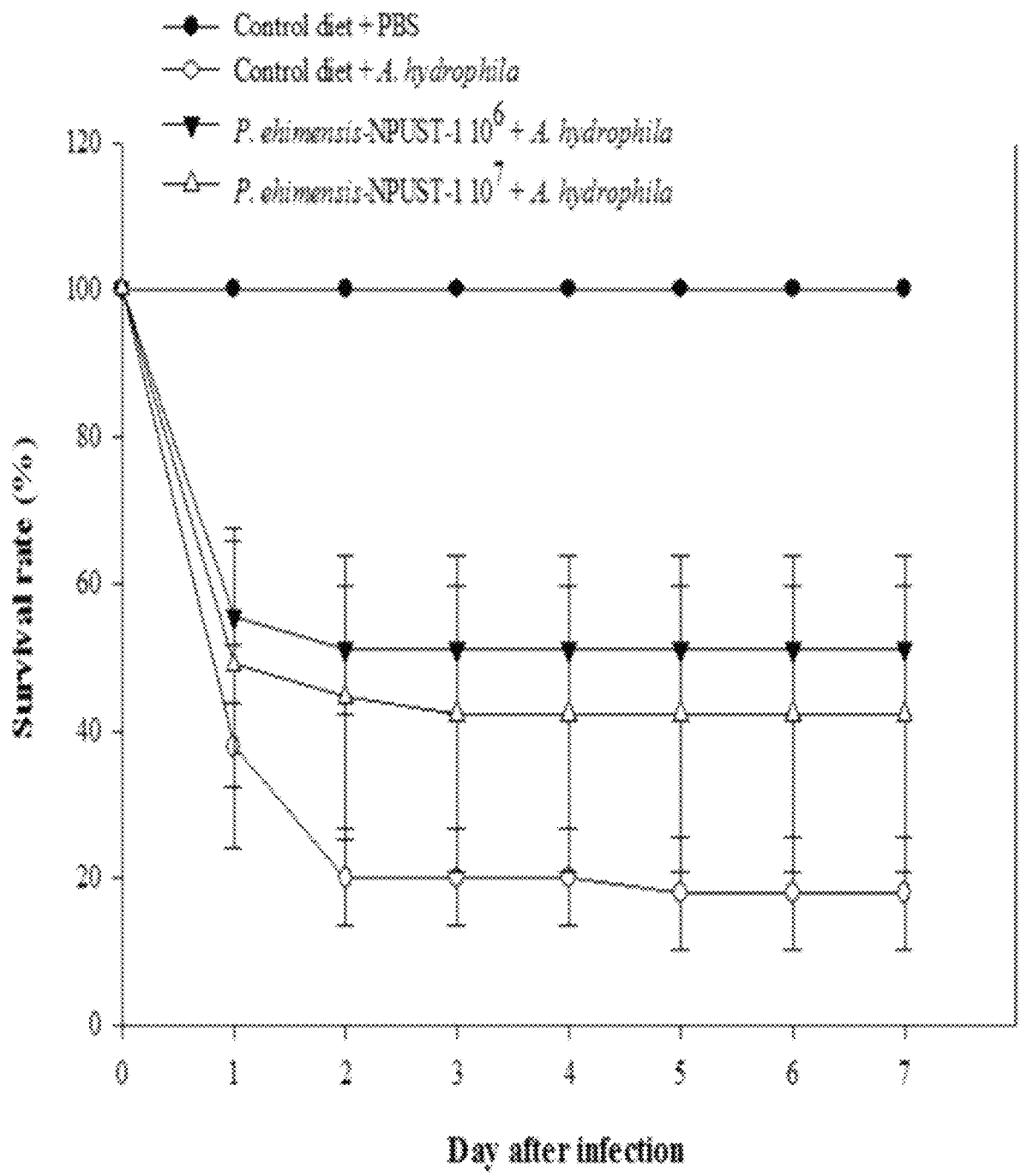
FIG. 20 shows comparative survival rate of tilapia treated with feed containing NPUST-1 after infected with *A. hydrophila*.

Results showed in FIG. 20 indicated that the survival rate of PBS injected blank group is 100%, whereas control group showed 16.1%, $1\times10^6$ CFU/g experimental 1 group fed with $1\times10^6$ CFU/g NPUST-1 showed 50.5% and $1\times10^7$ CFU/g fed experiment group 2 showed 38.5%. Thus it can be seen, by being fed to tilapia as probiotics, NPUST-1 showed efficacy of elevating survival rate of pathogen infected fish.

[Enhancement of Tilapia Macrophage Immune Response Via NPUST-1]

Macrophages play an important role in fish immune system. Therefore, further extract the macrophage of tilapia Inspected in aforementioned "Promotion of tilapia immune gene expression level via NPUST-1" experiment. Examine the expression of fish immunoregulation Indicators mentioned below in tilapia fed with NPUST-1 feeds: superoxidase dismutase (SOD) generation, phagocyte activity, respiratory burst and blood lysozyme activity. Steps of macrophages isolation and indicator expression examination are described below.

Isolation of macrophage: use different concentration of Percoll to separate macrophages by centrifugation. First, remove the head kidney of tilapia and wash with 1×PBS pH (7.6), place in 2 ml micro centrifuge, add 1 ml 1×PBS pH (7.6), homogenize the mixture with homogenizer and place on ice. Percoll concentration used is 28/51% (V/V). Prepare the 28% and 51% Percoll respectively, add 2 ml 28% Percoll to 15 ml micro centrifuge tube, then slowly inject 51% Percoll from bottom of 15 ml centrifuge tube to let 28% Percoll remain above and fully cover 51% Percoll, generating stratification. Next, slowly add 200~500 μl head kidney sample from above. Lastly, slowly add 1 ml 1×PBS pH (7.6) on top of the sample using 1 ml micro pipette to maintain clear 51% Percoll-28% Percoll|-head kidney sample-PBS stratification. Next, centrifuge the tube under 4° C. with the speed of 400×g for 30 minutes. After centrifugation, the macrophages will be intermediate between the two Percoll layers of different concentration. Extract the macrophage from nepheloid layer using micropipette and transfer to 1.7 ml micro centrifuge tube, then place on ice to maintain low temperature condition. Count the cells using a hemocytometer and dilute the macrophages to $1\times10^6$ cell/mi for following experiments.

Superoxidase dismutase analysis: first transfer 200 μl $1\times10^6$ cell/mi of macrophage suspension to 1.7 ml micro centrifuge tube. Mix 200 μl macrophage suspension with 500 μl HBSS thoroughly, place in centrifuge under 4° C. and centrifuge it for 20 minutes with the speed of 400×g. Remove the supernatant and add 5001 μl of HBSS, then centrifuge again. The steps are repeated three times to wash the macrophages. Resuspend the washed macrophages with 150 μl 1×PBS (pH 7.8), lyse the cells using ultrasonic processor and place in centrifuge under 4° C. and centrifuge it for 10 minutes with the speed of 1500×g. Extract the supernatant and determine sample protein concentration using Bio rad protein assay. Extract 100 μl of supernatant to 1.7 ml micro centrifuge tube then add 250 μl 0.15M Phosphatebuffer, 75 μl 0.13M Methionine, 75 μl 1 mM $Na_2$ EDTA, 75 μl 0.63 mM NBT and 150 μl 7.5 μM Riboflavin in sequence. Next, place in 25° C. incubation box for 10 minutes for reagent reaction. Extract 200 μl to 96 well plate after reaction and use spectrophotometer to determine $OD_{560}$ nm absorbance and sample absorbance. Determine the Superoxidase dismutase (SOD) value according to formula described below.

$$(Blank-Sample)/(Blank/2)\times6/Protein\ (mg) \qquad Formula:$$

SOD activity unit (U): One unit of SOD is defined as the amount of enzyme required to cause 50% inhibition of the Nitroblue tetrazolium (NBT) photoreduction rate Phagocyte activity (PA) analysis: this experiment needs to be proceeded in laminar flow, and the use of fluorescent beads shall avoid light. Fluorescent beads and povidone-iodine need to be prepared before the experiment. To prepare fluorescent beads, put 15 ml L-15 culture broth in 15 ml centrifuge tube then add 0.4 μl fluorescent beads. Povidone-iodine is prepared as 1 mg/ml by diluting with sterilized water. First transfer 300 μl macrophage sample to 12 well culture plate, stand for an hour for macrophage to be attached to the well, then discard the supernatant and add 300 μl L-15 culture broth to wash 3 times. After washing, add 300 μl prepared fluorescent beads, wrap the 12 well culture plate with aluminum foil and stand for 2 hours. After reaction, add 300 μl PBS to wash away majority of external fluorescent beads, then add 300 μl 1% Formaldehyde and fix the cell for 30 minutes. Wash away extra Formaldehyde with 300 μl PBS by 2-3 times, add 300 μl povidone-iodine and stain for 10 minutes. After staining, wash with 300 μl PBS twice and place under Olympus IX 50 fluorescence microscope to observe macrophage phagocytosis.

Respiratory burst ($O_2^-$) analysis of immune analysis: the group of this experiment comprises control group and experimental group. First extract 100 µl 0.2% Poly-L-Lysine to 96 well plate and stand for 30 minutes, then add 100 µl macrophage sample, centrifuge for 20 minutes at the speed of 300×g, remove the supernatant and add 100 µl MCBSS to the control group; add 100 µl Zymosan instead of MCBSS to the experiment group, and let both group stand for 30 minutes. After reaction is complete, remove the supernatant and wash with 100 µl MCHBSS 3 times, then add 100 µl 0.3% NTB to stain for 30 minutes. Add 100 µl 100% methanol to terminate the stain reaction, shake gently and remove the supernatant. Use 100 µl 70% methanol to wash 3 times, remove the supernatant and place on desk to dry for 20-30 minutes. Afterwards, add 120 µl 2M KOH and 140p DMSO, stand for 2 minutes, then use spectrophotometer to determine $OD_{630}$ nm absorbance.

Lysozyme Activity Analysis:

Use tilapia blood sample extracted from caudal peduncle by 25G needle and transfer the blood to 1.7 ml micro centrifuge tube, place the centrifuge tube angularly in 4° C. freezer for 24 hours to separate plasma and blood cells. Prepare 0.05M Sodiumphosphate buffer before the experiment, then use the buffer to prepare 1.6 mg/ml lysosome and 0.2 mg/ml *Mcicrococcus luteus* bacterial liquid. First, use lysosome as standard of experiment, dilute the lysosome to 0, 0.2, 0.4, 0.6, 0.8 and 1.6 mg/m, add 10 µl of lysozyme of each concentration into 96 well plate respectively and mix with 200 µl *M. luteus*. Use spectrophotometer to determine the $OD_{530}$ nm absorbance value at 1 minute from the beginning of reaction and 6 minutes from the beginning of reaction. Activity of lysosome are determined by change in OD values, the result values are generated into standard curve to estimate lysosome activity in following experiments. After the standard curve is obtained, start the blood samples analysis. Take out the blood samples already preserved in 4° C. freezer for 24 hours, centrifuge them for 5 minutes under 4° C. at the speed of 3000×g, transfer the plasma in upper layer to 1.7 ml micro centrifuge tube, then place on ice for the following lysosome analysis experiment, or preserve in −80° C. freezer. Repeat the previous step again to extract plasma of upper layer. Transfer 10 µl of plasma sample to 96 well plate, then add 200 µl *M. luteus* bacterial broth and mix. Use spectrophotometer to determine the $OD_{530}$ nm absorbance value at 1 minute from the beginning of reaction and 6 minutes from the beginning of reaction. Determine lysosome activity according to the OD value difference, and estimate the lysosome amount in plasma from standard curve.

Figure 21:
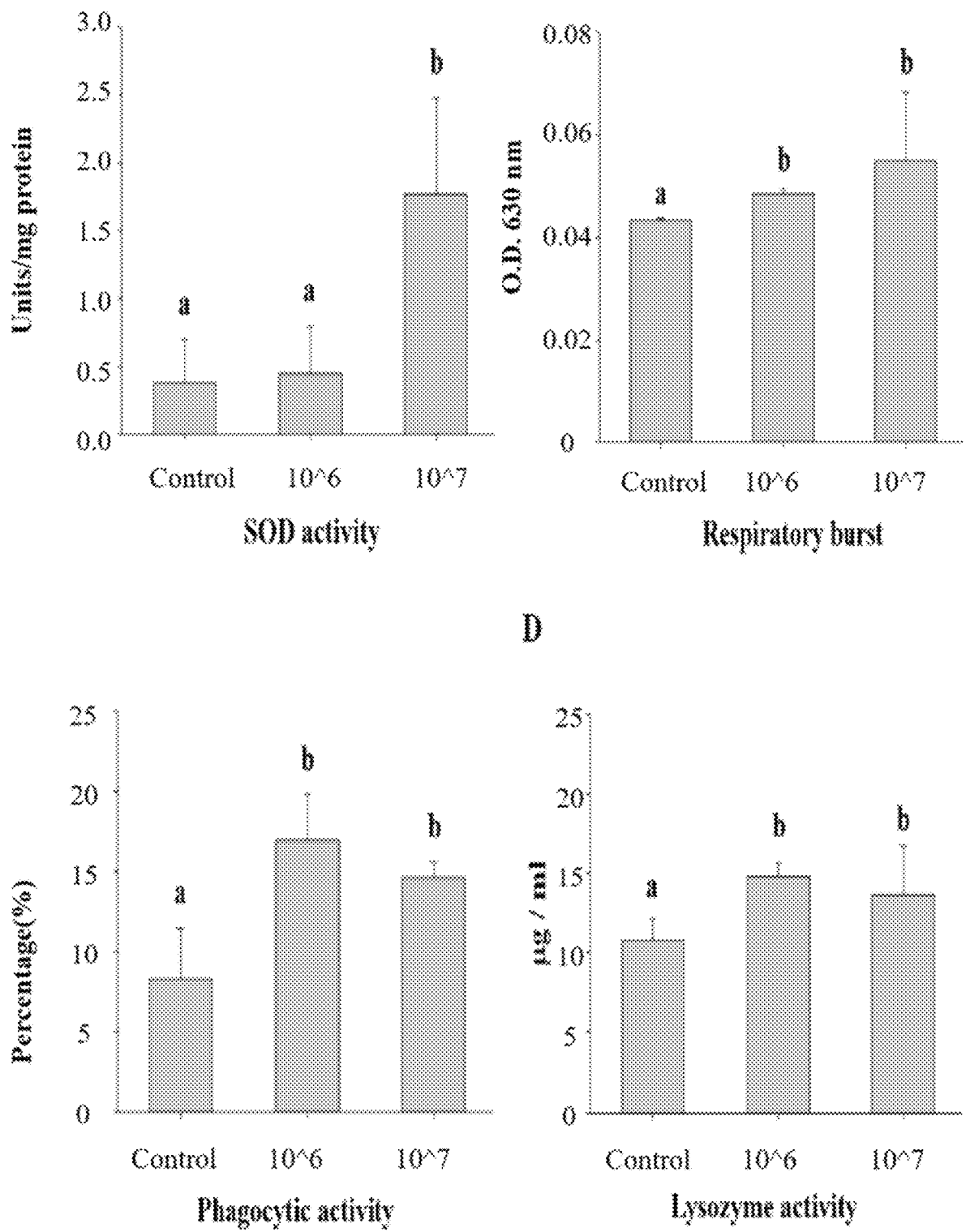
FIG. 21 shows comparative superoxide dismutase activity, respiratory burst, phagocytic activity and lysozyme level in blood among tilapia treated with feed containing NPUST-1.

Results showed in FIG. 21 indicated that among both of the NPUST1 $10^6$ CFU/g treated group and NPUST1 $10^7$ CFU/g treated group, the phagocytosis activity, respiratory burst and lysozyme activity have increased, while elevation of superoxidase dismutase expression is only recognized in the group fed with $10^7$ CFU/g *P. ehimensis* NPUST1. Thus it can be seen, by being fed to tilapia as probiotics, NPUST-1 showed efficacy of enhancing macrophage immune response of fish.

[Promotion of Tilapia Growth Via NPUST-1]

For each group of tilapia inspected in "Promotion of tilapia immune gene expression level via NPUST-1|", determine the body growth, feed conversion ratio and feed efficiency ratio to evaluate the efficacy of NPUST-1 on tilapia growth promotion. Detailed steps are described below.

Before feeding tilapia, measure the initial weight of fish (WI) in advance, then measure it weekly and adjust the feed according to the weight. Keep recording until the final weight of the fish (WF) at 2 month from beginning is obtained. Sum up the feed totally fed since beginning as total intake (F), and put the values into the formula below to calculate weight gain (WG), feed conversion ratio (FCR), feed efficiency ratio (FER) and specific growth rate (SGR).

WG=WF−WI

FCR=*F*/WF−WI

FER=WF−WI/*F*

SGR=(WF−WI)/feeding period×100      Formula:

Results in FIG. 7 showed that tilapia fed with $10^6$ CFU/g and $10^7$ CFU/g NPUST-1 has weight gain (WG) value of 47.46±1.85 g and 50.01±0.48 g respectively, which is significantly higher than value 29.63±0.46 g of control group fed without NPUST-1; feed conversion ratio (FCR) is 1.1 and 1.8 respectively, which is significantly better than the value 1.38 of control group value (fed without *P. ehimensis* NPUST-1); the feed efficiency ratio (Fernandes CF) is 0.91 and 0.92 respectively, which is significantly higher than value 0.73 of control group (fed without *P. ehimensis* NPUST-1). Thus it can be seen, by being fed to tilapia as probiotics, NPUST-1 showed efficacy of promoting fish body growth and feed efficiency.

TABLE 7

| Growth Value | Treated conditions (Feed contains NPUST-1 or not) | | |
|---|---|---|---|
| | Control | Containing $10^6$ CFU/g | Containing $10^7$ CFU/g |
| Initial weight (WI) | 5.53 ± 0.455 | 5.40 ± 0.475 | 5.57 ± 0.69 |
| Final weight (WF) | 37.25 ± 3.59 | 52.86 ± 2.32 | 55.58 ± 0.22 |
| Weight gain (WG) | 31.93 ± 3.53 | 47.46 ± 1.85 | 50.01 ± 0.48 |
| Survival rate (%) | 88.8 ± 3.85 | 95.56 ± 3.85 | 97.78 ± 3.85 |
| Feed conversion rate(FCR) | 1.38 ± 0.09 | 1.10 ± 0.04 | 1.08 ± 0.01 |
| Feed efficiency ratio | 0.73 ± 0.05 | 0.91 ± 0.04 | 0.92 ± 0.01 |
| Specific growth rate(%) | 57.02 ± 6.32 | 84.75 ± 3.31 | 89.30 ± 0.87 |

INDUSTRIAL APPLICABILITY

By being fed to aquaculture organisms as probiotics, the NPUST-1 strain of present invention can enhance immunoregulation and resistance against disease infection, hence lower the death rate of aquaculture organism.

On the other hand, the bacteriocin produced by the said strain of present invention, Peocin, has antibacterial effect on various aquaculture pathogens, foodborne pathogen and clinical drug-resistant pathogen. The said bacteriocin can be added into aquaculture feed to improve resistance against disease infection and lower the aquaculture organism death rate. Meanwhile, after the bacteriocin is purified into antibacterial protein, it has well storability under various environment, thus it can be a natural antibacterial additive for food or cosmetics to extend the preservation. Moreover, since the purified antibacterial protein shows antibacterial effect on antibiotic resistant pathogen MRSA, it can be further developed in healthcare industry as a protein drug to substitute antibiotics to treat drug resistant pathogenic infections. The technical means showed above are not seen in any other inventions in this technical field, hence the present invention is novel and innovative.

The above terms and explanations are included but not limited to demonstrate embodiments of the invention. Accordingly, this invention includes all embodiments, modifications and variations that contain technical features of the present invention without departing from the spirit and scope of the invention, and the scope thereof is determined by the appended claims.

What is claimed is:

1. A method of treating contamination of a food or cosmetic product by a pathogen, comprising applying an antimicrobial composition comprising a bacteriocin protein to the food or cosmetic product, wherein the bacteriocin protein is a DNA starvation/stationary phase protection protein produced by *Paenibacillus ehimensis* deposited with the China Center for Type Culture Collection under Accession No. M2018074, and wherein said bacteriocin protein has the amino acid sequence of SEQ ID NO: 1.

2. The method of claim 1, wherein the pathogen is one or more selected from the group consisting of *Aeromonas hydrophila, Vibrio vulnificus, Vibrio alginolyticus, Vibrio parahaenolyticus, Streptococcus agalactiae, Debaryonmyvces hansenii, Staphylococcus aureus*, Methicillin-resistant *Staphylococcus aureus* (MRSA), *Escherichia coli, Salmonella typhimurium, Listeria monocytogenes, Pseudomonas aeruginosa*, and *Burkholderia gladioli*.

3. The method of claim 1, wherein the pathogen is resistant to one or more antibiotics.

* * * * *

UNITED STATES PATENT AND TRADEMARK OFFICE
CERTIFICATE OF CORRECTION

PATENT NO. : 10,689,421 B2
APPLICATION NO. : 15/936443
DATED : June 23, 2020
INVENTOR(S) : Shao-Yang Hu It is certified that error appears in the above-identified patent and that said Letters Patent is hereby corrected as shown below:

On the Title Page

Column 2, Item (57) ABSTRACT, Line 2, delete "Paenibocillus" and insert -- Paenibacillus --

Column 2, Item (57) ABSTRACT, Line 6, delete "Paenibocillus" and insert -- Paenibacillus --

In the Specification

Column 1, Line 14, delete "9.783" and insert -- 9,783 --

In the Claims

Column 34, Line 50, Claim 2, delete "parahaenolyticus," and insert -- parahaemolyticus, --

Column 34, Lines 50-51, Claim 2, delete "Debaryonmyvces" and insert -- Debaryomyces --

Signed and Sealed this
First Day of September, 2020

Andrei Iancu
*Director of the United States Patent and Trademark Office*

```
                              SEQUENCE LISTING

<160> NUMBER OF SEQ ID NOS: 41

<210> SEQ ID NO 1
<211> LENGTH: 146
<212> TYPE: PRT
<213> ORGANISM: Paenibacillus ehimensis

<400> SEQUENCE: 1

Met Asn Glu Gln Leu Thr Val Leu Leu Asn Asn Gln Ile Ala Asn Trp
1               5                   10                  15

Ser Val Leu Tyr Val Lys Leu His Asn Tyr His Trp Tyr Val Lys Gly
            20                  25                  30

Pro Gln Phe Phe Thr Leu His Thr Lys Phe Glu Glu Leu Tyr Thr Glu
        35                  40                  45

Ala Ala Leu His Val Asp Ala Leu Ala Glu Arg Leu Leu Ala Leu Gly
    50                  55                  60

Gly Lys Pro Val Ala Thr Met Ser Gly Ser Leu Arg Leu Ala Ser Val
65                  70                  75                  80

Arg Glu Ala Glu Gly Glu Glu Ser Ala Glu Arg Met Val Ala Ala Leu
                85                  90                  95

Val Asn Asp Phe Thr Leu Ile Ile Gly Glu Leu Lys Ser Gly Met Lys
            100                 105                 110

Tyr Ala Glu Ser Val Gln Asp Glu Thr Thr Gly Asp Leu Leu Leu Ala
        115                 120                 125

Ile His Ser Ser Leu Glu Lys His Val Trp Met Leu Asn Ala Phe Leu
    130                 135                 140

Gly Asn
145

<210> SEQ ID NO 2
<211> LENGTH: 21
<212> TYPE: DNA
<213> ORGANISM: Artificial Sequence
<220> FEATURE:
<223> OTHER INFORMATION: Interleukin-1 beta PCR primer

<400> SEQUENCE: 2
tggacttcgc agcacaaaat g                                             21

<210> SEQ ID NO 3
<211> LENGTH: 20
<212> TYPE: DNA
<213> ORGANISM: Artificial Sequence
<220> FEATURE:
<223> OTHER INFORMATION: Interleukin-1 beta PCR primer

<400> SEQUENCE: 3
cacttcacgc tcttggatga                                               20

<210> SEQ ID NO 4
<211> LENGTH: 20
<212> TYPE: DNA
<213> ORGANISM: Artificial Sequence
<220> FEATURE:
<223> OTHER INFORMATION: Interleukin-6 PCR primer
```

<400> SEQUENCE: 4
tcaacttctc cagcgtgatg                                           20

<210> SEQ ID NO 5
<211> LENGTH: 21
<212> TYPE: DNA
<213> ORGANISM: Artificial Sequence
<220> FEATURE:
<223> OTHER INFORMATION: Interleukin-6 PCR primer

<400> SEQUENCE: 5
tctttccctc ttttcctcct g                                         21

<210> SEQ ID NO 6
<211> LENGTH: 20
<212> TYPE: DNA
<213> ORGANISM: Artificial Sequence
<220> FEATURE:
<223> OTHER INFORMATION: Interleukin-10 PCR primer

<400> SEQUENCE: 6
tcacgtcatg aacgagatcc                                           20

<210> SEQ ID NO 7
<211> LENGTH: 22
<212> TYPE: DNA
<213> ORGANISM: Artificial Sequence
<220> FEATURE:
<223> OTHER INFORMATION: Interleukin-10 PCR primer

<400> SEQUENCE: 7
cctcttgcat ttcaccatat cc                                        22

<210> SEQ ID NO 8
<211> LENGTH: 24
<212> TYPE: DNA
<213> ORGANISM: Artificial Sequence
<220> FEATURE:
<223> OTHER INFORMATION: Interleukin-15 PCR primer

<400> SEQUENCE: 8
atgtcattgg aactcagagg tttg                                      24

<210> SEQ ID NO 9
<211> LENGTH: 22
<212> TYPE: DNA
<213> ORGANISM: Artificial Sequence
<220> FEATURE:
<223> OTHER INFORMATION: Interleukin-15 PCR primer

<400> SEQUENCE: 9
ctgttctgga tgtcctgctt ga                                        22

<210> SEQ ID NO 10
<211> LENGTH: 24
<212> TYPE: DNA
<213> ORGANISM: Artificial Sequence
<220> FEATURE:
<223> OTHER INFORMATION: Interleukin-21 PCR primer

<400> SEQUENCE: 10
aatcattcat cgtggacagt gtgt                                      24

<210> SEQ ID NO 11
<211> LENGTH: 20

```
<212> TYPE: DNA
<213> ORGANISM: Artificial Sequence
<220> FEATURE:
<223> OTHER INFORMATION: Interleukin-21 PCR primer

<400> SEQUENCE: 11
aacgttcggc tgttgaccat                                              20

<210> SEQ ID NO 12
<211> LENGTH: 20
<212> TYPE: DNA
<213> ORGANISM: Artificial Sequence
<220> FEATURE:
<223> OTHER INFORMATION: Tumor necrosis factor-alpha PCR primer

<400> SEQUENCE: 12
aaggagagtt gcctttaccg                                              20

<210> SEQ ID NO 13
<211> LENGTH: 19
<212> TYPE: DNA
<213> ORGANISM: Artificial Sequence
<220> FEATURE:
<223> OTHER INFORMATION: Tumor necrosis factor-alpha PCR primer

<400> SEQUENCE: 13
attgccctgg gtcttatgg                                               19

<210> SEQ ID NO 14
<211> LENGTH: 20
<212> TYPE: DNA
<213> ORGANISM: Artificial Sequence
<220> FEATURE:
<223> OTHER INFORMATION: Interferon-gamma PCR primer

<400> SEQUENCE: 14
gagaggctgg cacatgttca                                              20

<210> SEQ ID NO 15
<211> LENGTH: 21
<212> TYPE: DNA
<213> ORGANISM: Artificial Sequence
<220> FEATURE:
<223> OTHER INFORMATION: Interferon-gamma PCR primer

<400> SEQUENCE: 15
cccatagcgt ttctgcatac g                                            21

<210> SEQ ID NO 16
<211> LENGTH: 22
<212> TYPE: DNA
<213> ORGANISM: Artificial Sequence
<220> FEATURE:
<223> OTHER INFORMATION: Nuclear factor-kB PCR primer

<400> SEQUENCE: 16
aagaggacca aaataagcac ag                                           22

<210> SEQ ID NO 17
<211> LENGTH: 23
<212> TYPE: DNA
<213> ORGANISM: Artificial Sequence
<220> FEATURE:
<223> OTHER INFORMATION: Nuclear factor-kB PCR primer

<400> SEQUENCE: 17
```
aagtccaagg tacatcgcca tga                                              23

<210> SEQ ID NO 18
<211> LENGTH: 20
<212> TYPE: DNA
<213> ORGANISM: Artificial Sequence
<220> FEATURE:
<223> OTHER INFORMATION: Cyclooxygenase-2 alpha PCR primer

<400> SEQUENCE: 18
gatctcccaa atgccaagca                                                  20

<210> SEQ ID NO 19
<211> LENGTH: 20
<212> TYPE: DNA
<213> ORGANISM: Artificial Sequence
<220> FEATURE:
<223> OTHER INFORMATION: Cyclooxygenase-2 alpha PCR primer

<400> SEQUENCE: 19
gggcgaagaa agcaaacatg                                                  20

<210> SEQ ID NO 20
<211> LENGTH: 21
<212> TYPE: DNA
<213> ORGANISM: Artificial Sequence
<220> FEATURE:
<223> OTHER INFORMATION: Cyclooxygenase-2 beta PCR primer

<400> SEQUENCE: 20
gagctgccag acgtgaagat g                                                21

<210> SEQ ID NO 21
<211> LENGTH: 20
<212> TYPE: DNA
<213> ORGANISM: Artificial Sequence
<220> FEATURE:
<223> OTHER INFORMATION: Cyclooxygenase-2 beta PCR primer

<400> SEQUENCE: 21
gggcgaagaa agcgaacata                                                  20

<210> SEQ ID NO 22
<211> LENGTH: 21
<212> TYPE: DNA
<213> ORGANISM: Artificial Sequence
<220> FEATURE:
<223> OTHER INFORMATION: Complement component c3b PCR primer

<400> SEQUENCE: 22
cgtctccgta caccatccat t                                                21

<210> SEQ ID NO 23
<211> LENGTH: 23
<212> TYPE: DNA
<213> ORGANISM: Artificial Sequence
<220> FEATURE:
<223> OTHER INFORMATION: Complement component c3b PCR primer

<400> SEQUENCE: 23
ggcgtctcat caggatttgt tac                                              23

<210> SEQ ID NO 24
<211> LENGTH: 21
<212> TYPE: DNA
<213> ORGANISM: Artificial Sequence

```
<220> FEATURE:
<223> OTHER INFORMATION: Lysozyme PCR primer

<400> SEQUENCE: 24
cgtggatgtc ctcgtgtgaa g                                     21

<210> SEQ ID NO 25
<211> LENGTH: 20
<212> TYPE: DNA
<213> ORGANISM: Artificial Sequence
<220> FEATURE:
<223> OTHER INFORMATION: Lysozyme PCR primer

<400> SEQUENCE: 25
ccaatggaga atccctcaaa                                       20

<210> SEQ ID NO 26
<211> LENGTH: 21
<212> TYPE: DNA
<213> ORGANISM: Artificial Sequence
<220> FEATURE:
<223> OTHER INFORMATION: Toll-like receptor-1 PCR primer

<400> SEQUENCE: 26
cagagcgaat ggtgccacta t                                     21

<210> SEQ ID NO 27
<211> LENGTH: 20
<212> TYPE: DNA
<213> ORGANISM: Artificial Sequence
<220> FEATURE:
<223> OTHER INFORMATION: Toll-like receptor-1 PCR primer

<400> SEQUENCE: 27
gtggcagagg ctccagaaga                                       20

<210> SEQ ID NO 28
<211> LENGTH: 22
<212> TYPE: DNA
<213> ORGANISM: Artificial Sequence
<220> FEATURE:
<223> OTHER INFORMATION: Toll-like receptor-3 PCR primer

<400> SEQUENCE: 28
tggagcatca cagggataaa ga                                    22

<210> SEQ ID NO 29
<211> LENGTH: 20
<212> TYPE: DNA
<213> ORGANISM: Artificial Sequence
<220> FEATURE:
<223> OTHER INFORMATION: Toll-like receptor-3 PCR primer

<400> SEQUENCE: 29
tgatgcccat gcctgtaaga                                       20

<210> SEQ ID NO 30
<211> LENGTH: 18
<212> TYPE: DNA
<213> ORGANISM: Artificial Sequence
<220> FEATURE:
<223> OTHER INFORMATION: Toll-like receptor-4 alpha PCR primer

<400> SEQUENCE: 30
tgcctggtgt cgctttga                                         18
```

```
<210> SEQ ID NO 31
<211> LENGTH: 20
<212> TYPE: DNA
<213> ORGANISM: Artificial Sequence
<220> FEATURE:
<223> OTHER INFORMATION: Toll-like receptor-4 alpha PCR primer

<400> SEQUENCE: 31
cctctccgca acatcttcca                                                   20

<210> SEQ ID NO 32
<211> LENGTH: 20
<212> TYPE: DNA
<213> ORGANISM: Artificial Sequence
<220> FEATURE:
<223> OTHER INFORMATION: Toll-like receptor-9 PCR primer

<400> SEQUENCE: 32
cggacaccca gtatgatgca                                                   20

<210> SEQ ID NO 33
<211> LENGTH: 19
<212> TYPE: DNA
<213> ORGANISM: Artificial Sequence
<220> FEATURE:
<223> OTHER INFORMATION: Toll-like receptor-9 PCR primer

<400> SEQUENCE: 33
ccccggttct ccaatctca                                                    19

<210> SEQ ID NO 34
<211> LENGTH: 23
<212> TYPE: DNA
<213> ORGANISM: Artificial Sequence
<220> FEATURE:
<223> OTHER INFORMATION: MX PCR primer

<400> SEQUENCE: 34
gagtttcgac cttggcacag aga                                               23

<210> SEQ ID NO 35
<211> LENGTH: 21
<212> TYPE: DNA
<213> ORGANISM: Artificial Sequence
<220> FEATURE:
<223> OTHER INFORMATION: MX PCR primer

<400> SEQUENCE: 35
ctggtcagct agacgcttgc t                                                 21

<210> SEQ ID NO 36
<211> LENGTH: 22
<212> TYPE: DNA
<213> ORGANISM: Artificial Sequence
<220> FEATURE:
<223> OTHER INFORMATION: Elongation factor 1 alpha PCR primer

<400> SEQUENCE: 36
aacagctgat cgttggagtc aa                                                22

<210> SEQ ID NO 37
<211> LENGTH: 22
<212> TYPE: DNA
<213> ORGANISM: Artificial Sequence
<220> FEATURE:
<223> OTHER INFORMATION: Elongation factor 1 alpha PCR primer
```

```
<400> SEQUENCE: 37
ttgatgtatg cgctgacttc ct                                              22

<210> SEQ ID NO 38
<211> LENGTH: 22
<212> TYPE: DNA
<213> ORGANISM: Artificial Sequence
<220> FEATURE:
<223> OTHER INFORMATION: Tumor necrosis factor-alpha PCR primer

<400> SEQUENCE: 38
ccagaagcac taaaggcgaa ga                                              22

<210> SEQ ID NO 39
<211> LENGTH: 20
<212> TYPE: DNA
<213> ORGANISM: Artificial Sequence
<220> FEATURE:
<223> OTHER INFORMATION: Tumor necrosis factor-alpha PCR primer

<400> SEQUENCE: 39
ccttggcttt gctgctgatc                                                 20

<210> SEQ ID NO 40
<211> LENGTH: 21
<212> TYPE: DNA
<213> ORGANISM: Artificial Sequence
<220> FEATURE:
<223> OTHER INFORMATION: Transforming growth factor-beta PCR primer

<400> SEQUENCE: 40
gtttgaactt cggcggtact g                                               21

<210> SEQ ID NO 41
<211> LENGTH: 21
<212> TYPE: DNA
<213> ORGANISM: Artificial Sequence
<220> FEATURE:
<223> OTHER INFORMATION: Transforming growth factor-beta PCR primer

<400> SEQUENCE: 41
tcctgctcat agtcccagag a                                               21
```